United States Patent [19]

Spencer et al.

[11] Patent Number: 5,770,433
[45] Date of Patent: Jun. 23, 1998

[54] RECOMBINANT 47 AND 31KD COCOA PROTEINS AND PRECURSOR

[75] Inventors: Margaret Elizabeth Spencer, Sheffield; Rachel Hodge, Leicester; Edward Alfred Deakin; Sean Ashton, both of Sheffield, all of England

[73] Assignee: Mars U.K. Limited, Berkshire, England

[21] Appl. No.: 955,905

[22] PCT Filed: Jun. 7, 1991

[86] PCT No.: PCT/GB91/00914

§ 371 Date: Jan. 21, 1993

§ 102(e) Date: Jan. 21, 1993

[87] PCT Pub. No.: WO91/19801

PCT Pub. Date: Dec. 26, 1991

[30] Foreign Application Priority Data

Jun. 11, 1990 [GB] United Kingdom ................... 9013016

[51] Int. Cl.⁶ .............................. C12N 5/00; A23J 3/14; C07K 14/415
[52] U.S. Cl. .................. 435/252.33; 530/370; 536/23.6; 435/69.1; 435/254.21; 435/320.1; 426/534; 426/656
[58] Field of Search ..................... 530/377, 370; 536/23.6; 435/320.1, 69.1, 240.1, 252.3, 252.31, 255, 252.33, 254.21; 426/534, 656

[56] References Cited

U.S. PATENT DOCUMENTS 4,289,690 9/1981 Restka et al. ........................... 530/351

FOREIGN PATENT DOCUMENTS 0206783 12/1986 European Pat. Off. .

OTHER PUBLICATIONS

Matsudairo, 1987. J. Biol. Chem. 262(21): 10035–10038.

Wozney, J.M. 1990. Methods in Enzymology 182: 738–749.

Watson, James P. 1987. *Molecular Biology of the Genes* The Benjamin/Cummings Publishing Company, Inc.

Biehl et al., J. Sci. Food Agric. 33, 1291–1304 (1982);

Fritz et al., Journal of Food Science 50, 946–950 (1985);

Pettipher, Café Cacao Thé, vol. XXXIV, No. 1, 22–26 (1990);

Wilson et al., Abstr. Pap. Am. Chem. Soc., #148 (1984);

Chlan et al., Plant Molecular Biology 9, 533–546 (1987);

Chemical Abstracts, vol. 109, p. 210 (1988);

Cramer et al., Proc. Natl. Acad. Sci. USA 82, 334–338 (1985);

Chemical Abstracts, vol. 106, p. 286 (1987); and

Higgins et al., Plant Molecular Biology 11, 683–695 (1988).

*Primary Examiner*—Lorraine M. Spector
*Attorney, Agent, or Firm*—Leonard J. Santisi

[57] ABSTRACT

47 kD and 31 kD proteins, and their 67 kD expression precursor, believed to be the source of peptide flavour precursors in cocoa (*Theobroma cacao*) have been identified. Genes coding for them have been probed, identified and sequenced, and recombinant proteins have been synthesised.

14 Claims, 22 Drawing Sheets

FIG. 2A

```
              M   V   I   S   K   S   P   F   I   V   L   I   F   S   L   L
AAGCATAGCAAATATGGTGATCAGTAAGTCTCCTTTCATAGTTTTGATCTTCTCTTCT
              10              20              30              40              50              60

L   S   F   A   L   L   C   S   G   V   S   A   Y   G   R   K   Q   Y   E   R
CCTTTCTTTTGCGTTGCTTGTTCTGGTGTGTCAGCGCCTATGGCAGAAACAATATGAGCG
              70              80              90             100             110             120

D   P   R   Q   Q   Y   E   Q   C   Q   R   R   C   E   S   E   A   T   E   E
TGATCCTCGACAGCAATACGAGCAATGCCAGAGGCGATGCCAGTCGGAAGCGACTGAAGA
             130             140             150             160             170             180

R   E   Q   C   E   Q   R   C   E   R   E   Y   K   E   Q   Q   R   Q
AAGGGAGCAAGAGAGCAGTGTGAACAACGCTGTGAAAGGAGTACAAGGAGCAGCAGAGACA
             190             200             210             220             230             240

Q   E   E   E   L   Q   R   Q   Y   Q   Q   C   Q   G   R   C   Q   E   Q   Q
GCAAGAAGAGAGCTTCAAGAGGCAATACCAGCAATGTCAAGGGCCGTTGTCAAGAGCAACA
             250             260             270             280             290             300

Q   G   Q   R   E   Q   Q   Q   Q   C   Q   R   K   C   W   E   Q   Y   K   E   Q
ACAGGGGCAGAGAGAGCAGCAGTGCCAGAGAAAATGCTGGGAGCAATATAAGGAACA
             310             320             330             340             350             360

E   R   G   E   H   E   N   Y   H   N   H   K   K   N   R   S   E   E   E   E
AGAGAGAGGCGAGCACGAGAATTACCATAATCACAAAAAATAGGAGCGAAGAAGAAGA
             370             380             390             400             410             420

G   Q   Q   R   N   N   P   Y   Y   F   P   K   R   R   S   F   Q   T   R   F
AGGGCAACAAAGAAACAATCCTTACTATTTCCTAAAAGAGATCATTCCAAACTCGATT
             430             440             450             460             470             480
```

FIG. 2B

```
  R   D   E   E   G   N   F   K   I   L   Q   R   F   A   E   N   S   P   P   L
CAGGGATGAAGAGGGCAACTTCAAGATCCTCCAGAGGTTTGCTGAGAACTCTCCTCCACT
          490                 500                 510                 520                 530                 540

K   G   I   N   D   Y   R   L   A   M   F   E   A   N   P   N   T   F   I   L
CAAGGGCATCAACGATTACCGCCTTGGCCATGTTCGAAGCAAATCCCAACACTTTTATTCT
          550                 560                 570                 580                 590                 600

P   H   H   C   D   A   E   A   I   Y   F   V   T   N   G   K   G   T   I   T
TCCGCACCACTGTGATGCTGAGGCAATTTACTTCGTGACAAACGGAAAGGGACAATTAC
          610                 620                 630                 640                 650                 660

F   V   T   H   E   N   K   E   S   Y   N   V   Q   R   G   T   V   V   S   V
GTTTGTGACTCATGAAAACAAAGAGTCCTATAATGTACAGCGTGGAACAGTAGTCAGCGT
          670                 680                 690                 700                 710                 720

P   A   G   S   T   V   V   Y   V   V   S   Q   D   N   Q   E   K   L   T   I   A
TCCTGCAGGAAGCACTGTTACGTGTTAGCCAAGACAACCAAGAAGCTAACCATAGC
          730                 740                 750                 760                 770                 780

V   L   A   L   P   V   N   S   P   G   K   Y   E   L   F   F   P   A   G   N
TGTGCTCGCCCTGCCCGTTAATTCTCCTGGCAAATATGAGTTATTCTTCCCCGCTGGAAA
          790                 800                 810                 820                 830                 840

N   K   P   E   S   Y   Y   G   A   F   S   Y   E   V   L   E   T   V   F   N
TAATAAACCTGAATCATATTACGGAGCCTTCAGCTATGAAGTTCTTGAGACCGTCTTCAA
          850                 860                 870                 880                 890                 900

T   Q   R   E   K   L   E   E   I   L   E   E   Q   R   G   Q   K   R   Q   Q
TACACAAAGAGAAAGCTGGAGGAGATCTTGGAGGAACAGAGAGGGCAGAAGAGGCAGCA
          910                 920                 930                 940                 950                 960
```

FIG. 2C

```
  G   Q   Q   G   M   F   R   K   A   K   P   E   Q   I   R   A   I   S   Q   Q
GGGGCAGCAGGGTATGTTCCGGAAAAGCCAAACCAGAGAGCAGATAAGAGCAATAAGCCAACA
        970           980           990          1000          1010          1020

A   T   S   P   R   H   R   G   G   E   R   L   A   I   N   L   L   S   Q   S
AGCTACTTCTCCAAGGCACAGAGAGGCGGGGGAGAGACTTGCCATCAATCTATTGAGCCAATC
       1030          1040          1050          1060          1070          1080

P   V   Y   S   N   Q   N   G   R   F   F   E   A   C   P   E   D   F   S   Q
GCCTGTGTCTACTCCAACCAAAACGGACGCTTCTTTGAGGCTTGTCCTGAGGACTTCAGTCA
       1090          1100          1110          1120          1130          1140

F   Q   N   M   D   V   A   V   S   A   F   K   L   N   Q   G   A   I   F   V
ATTTCAGAACATGGATGTCGCTGTTTCAGCCTTCAAACTGAATCAGGGAGCCATATTTGT
       1150          1160          1170          1180          1190          1200

P   H   Y   N   S   K   A   T   F   V   V   F   V   T   D   G   Y   G   Y   A
GCCACACTACAATTCTAAGGCTACATTCGTGGTTGTCCACGGACGGATATGGGTACGC
       1210          1220          1230          1240          1250          1260

Q   M   A   C   P   H   L   S   R   Q   S   Q   G   S   Q   S   G   R   Q   D
TCAAATGGCTTGCCCGCCATCTCTCCAGACAGAGCCAGGGATCCCAAAGTGGAAGGCAAGA
       1270          1280          1290          1300          1310          1320

R   R   E   Q   E   E   E   S   E   E   E   T   F   G   E   F   Q   Q   V   K
CAGAAGAGAACAAGAAGAGTCAGAAGAGGAGACATTTGGAGAATTCCAGCAGGTCAA
       1330          1340          1350          1360          1370          1380

A   P   L   S   P   G   D   V   F   V   A   P   A   G   H   A   V   T   F   F
AGCCCCATTGTCACCTGGTGACGTCTTTGTAGCCCCGGCCAGGCCATGCAGTTACATTCTT
       1390          1400          1410          1420          1430          1440
```

FIG. 2D

```
      A   S   K   D   Q   P   L   N   A   V   A   F   G   L   N   A   Q   N   N   Q
    TGCATCCAAAGACCAGCCCCTGAATGCAGTTGCGTTTGGACTCAACGCCCAGAACAACCA
              1450        1460        1470        1480        1490        1500

R   I   F   L   A   G   K   K   N   L   V   R   Q   M   D   S   E   A   K   E
    GAGAATTTCCTTGCAGGGAAAAAGAACTTGGTCAGACAAATGGATAGCGAGGCAAAGGA
              1510        1520        1530        1540        1550        1560

L   S   F   G   V   P   S   K   L   V   D   N   I   F   N   N   P   D   E   S
    GTTATCATTTGGGGTACCATCGAAATTGGTAGATAATATATTCAACAACCCGGATGAGTC
              1570        1580        1590        1600        1610        1620

Y   F   M   S   F   S   Q   Q   R   Q   R   D   E   R   R   G   N   P   L
    GTATTTCATGTCTTTCTCTCAACAGAGGCAGCGTCGAGATGAAAGGAGGGGCAATCCCTT
              1630        1640        1650        1660        1670        1680

A   S   I   L   D   F   A   R   L   F   *
    GGCCTCAATTCTGGACTTTGCCCGGCTTGTTCTAAGCAGCTGCTTCCACTTTTGTATCAGA
              1690        1700        1710        1720        1730        1740

CATGCAGAGGCATGTAATGCAATAAATAAGTTGGCCTATGTAAAGAGGAGAGTTTGCT
              1750        1760        1770        1780        1790        1800

TTTGTCTTGTTCTAACCTTGTTTTGAACTAGTAAACTTTCAATGTAATGAGAGTTGTTAT
              1810        1820        1830        1840        1850        1860

CTTTCTA
```

FIG. 3

```
         10         20         30         40         50         60
MVISKSPFIV LIFSLLLSFA LLCSGVSAYG RKQYERDPRQ QYEQCQRRCE SEATEEREQE
         70         80         90        100        110        120
QCEQRCEREY KEQQRQQEEE LQRQYQQCQG RCQEQQQGQR EQQQCQRKCW EQYKEQERGE
        130        140        150        160        170        180
           EEPGSQF ANPAYHF
HENYHNHKKN RSEEEGQQR NNPYYFPKRR SFQTRFRDEE GNFKILQRFA ENSPPLKGIN
        190        200        210        220        230        240
DYRLAMFEAN PNTFILPHHC DAEAIYFVTN GKGTITFVTH ENKESYNVQR GTVVSVPAGS
        250        260        270        280        290        300
TVYVVSQDNQ EKLTIAVLAL PVNSPGKYEL FFPAGNNKPE SYYGAFSYEV LETVFNTQRE
        310        320        330        340        350        360
KLEEILEEQR GQKRQQGQQG MFRKAKPEQI RAISQQATSP RHRGGERLAI NLLSQSPVYS
        370        380        390        400        410        420
NQNGRFFEAC PEDFSQFQNM DVAVSAFKLN QGAIFVPHYN SKATFVVFVT DGYGYAQMAC
        430        440        450        460        470        480
PHLSRQSQGS QSGRQDRREQ EEESEEETFG EFQQVKAPLS PGDVFVAPAG HAVTFFASKD
        490        500        510        520        530        540
QPLNAVAFGL NAQNNQRIFL AGKKNLVRQM DSEAKELSFG VPSKLVDNIF NNPDESYFMS
        550        560        570                580        590        600
FSQQRRRDE RRGNPLASIL DFARLF
```

FIG. 4D (Sequence alignment figure - sheet 10 of 22)

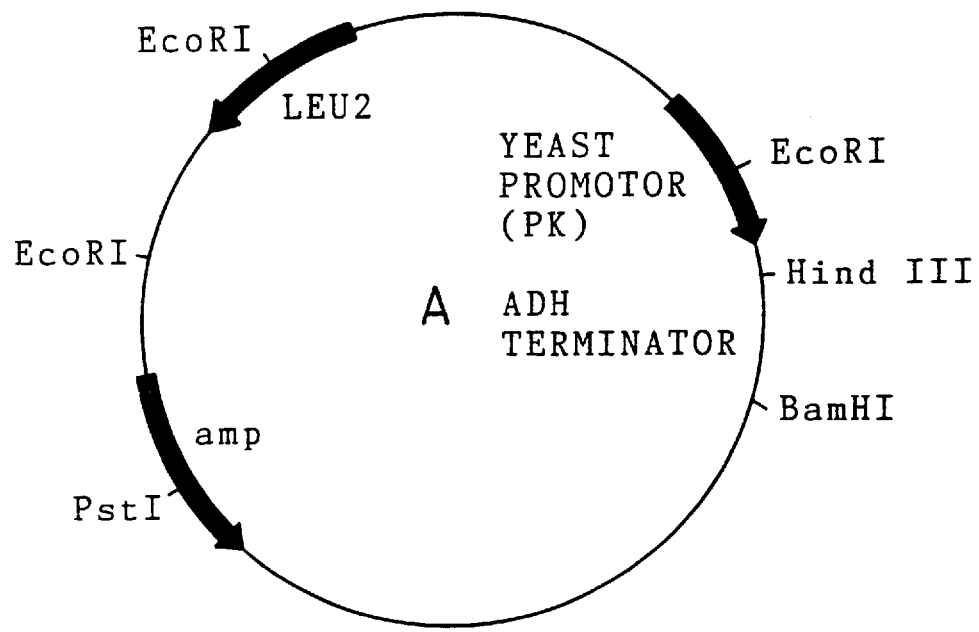
FIG. 7
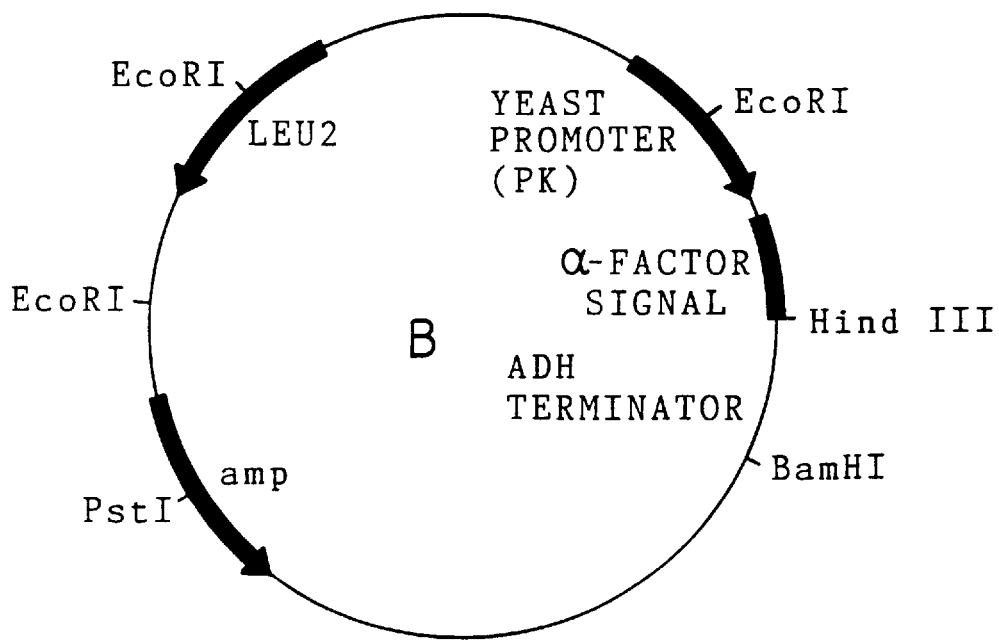

FIG. 8A

YEAST PYRUVATE
KINASE GENE

```
                                              MetSerArg
TTTACAAGACACCAATCAAATAAACAATCATCACAATGTCAATGTCTAGA
```

↓

SEQUENCE ALTERED
TO CREATE CLONING
SITE

```
                                              MetSerArg
TTTACAAGCTTCCAATCAAAACAATAAACATCATCACAATGTCTAGA
        ───
        Hin
```

+

HIN-NCO LINKERS

```
AGCTTCCAATCAAAACAAATAAAACATCATCAC
AGGTTAGTTTTGTTTATTTTGTAGTAGTGGTAC
```

↓

67kD EXPRESSION
VECTOR A

```
                                              MetValIle
TTTACAAGCTTCCAATCAAAACAAATAAACATCATCACCATGGTGATC
        ───                              ─────
        Hin                               Nco
```

FIG. 8B

YEAST ALPHA-FACTOR
SIGNAL SEQUENCE

```
          1          231
        Met----GluGlyValSerLeuAspLysArgGlu
        ATG----GAAGGGGTAAGCTTGGATAAAAGAGAG
                       _____
                           Hin
```

HIN-NCO LINKERS

```
        AGCTTGGATAAAAGAGC
            ACCTATTTTCTCGGTAC
```

IN-PHASE FUSION OF
67KD CODING REGION

```
        Met----GluGlyValSerLeuAspLysArgAlaMetAlaLeu
        ATG----GAAGGGGTAAGCTTGGATAAAAGAGAGCCATGGCGTTG
                       _____         _____
                           Hin                Nco
```

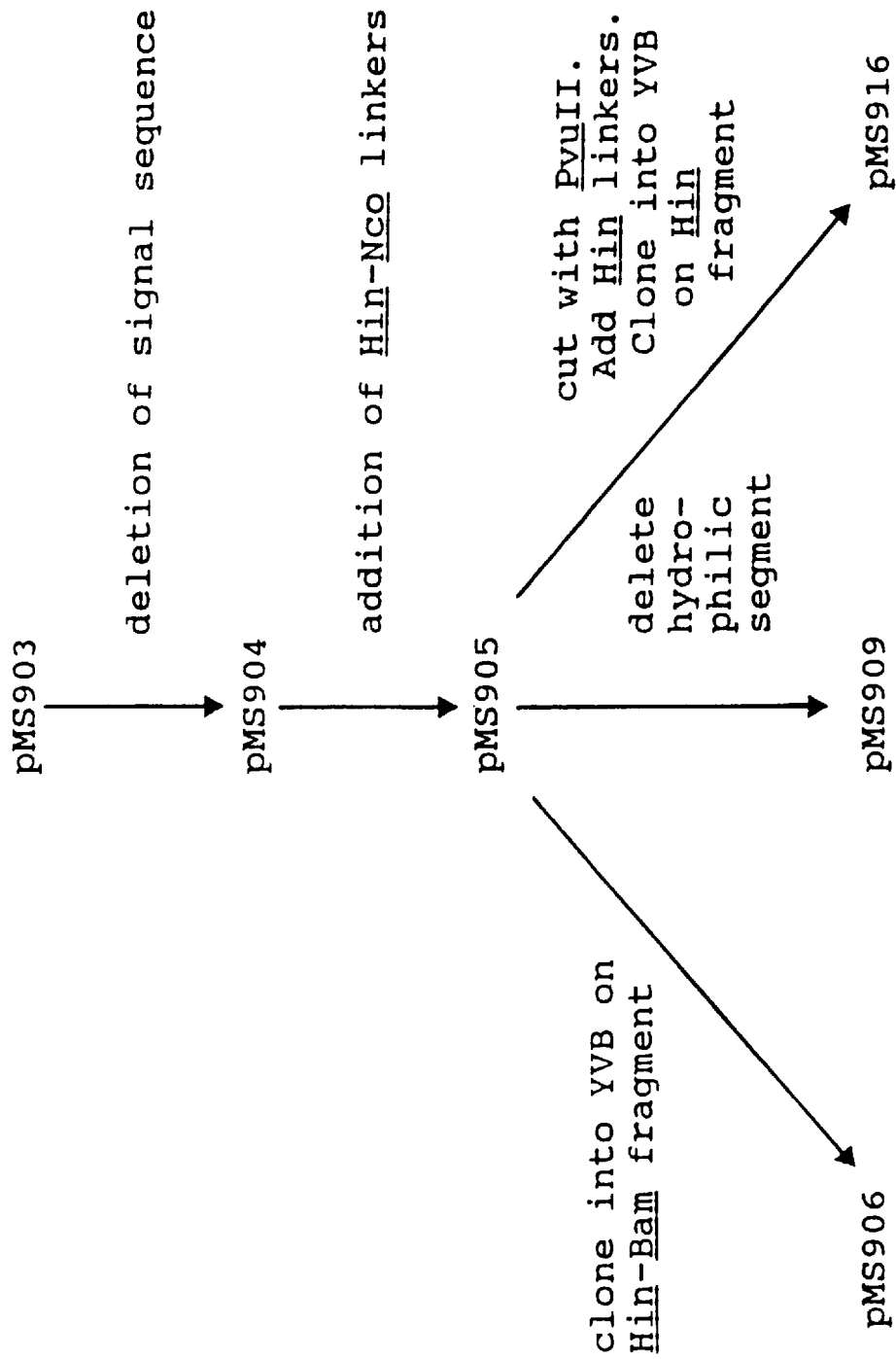

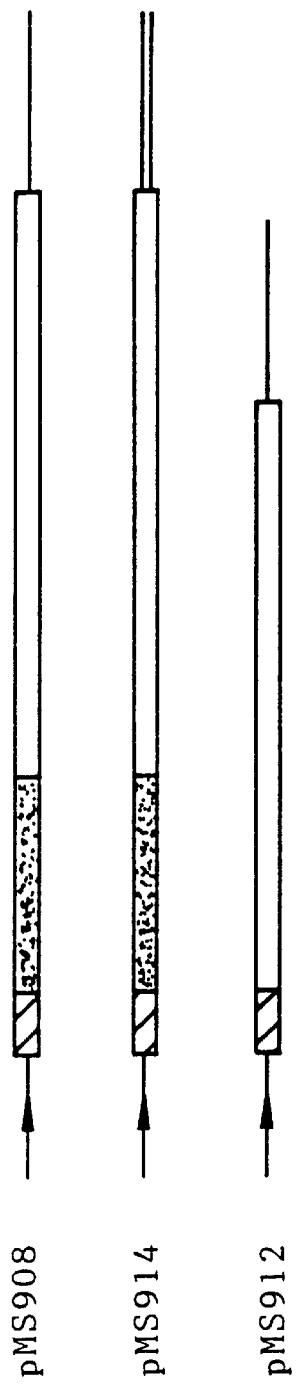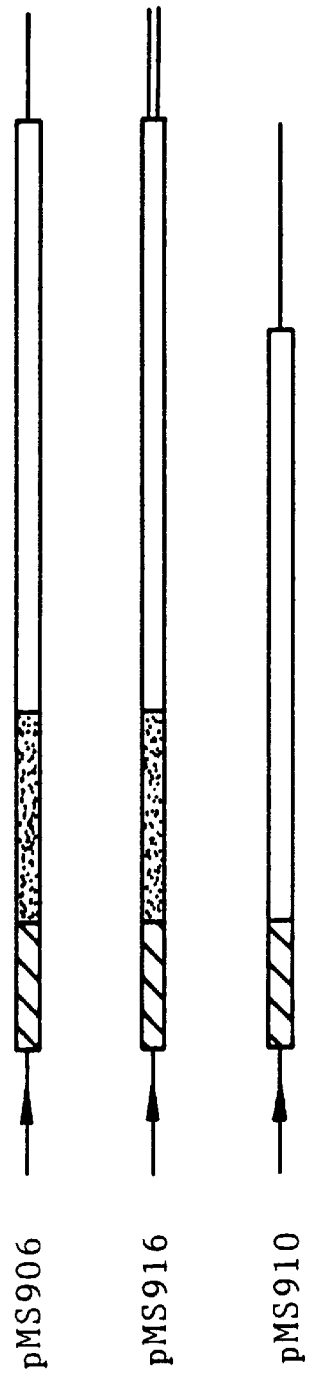
FIG. 10

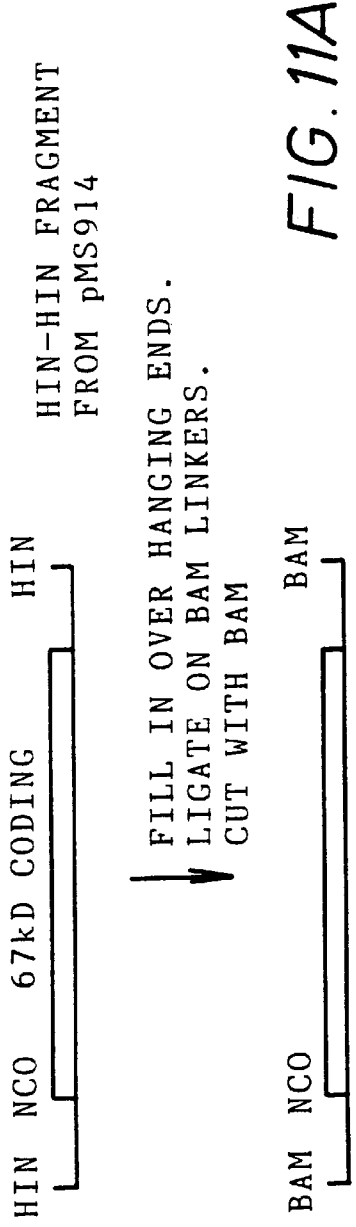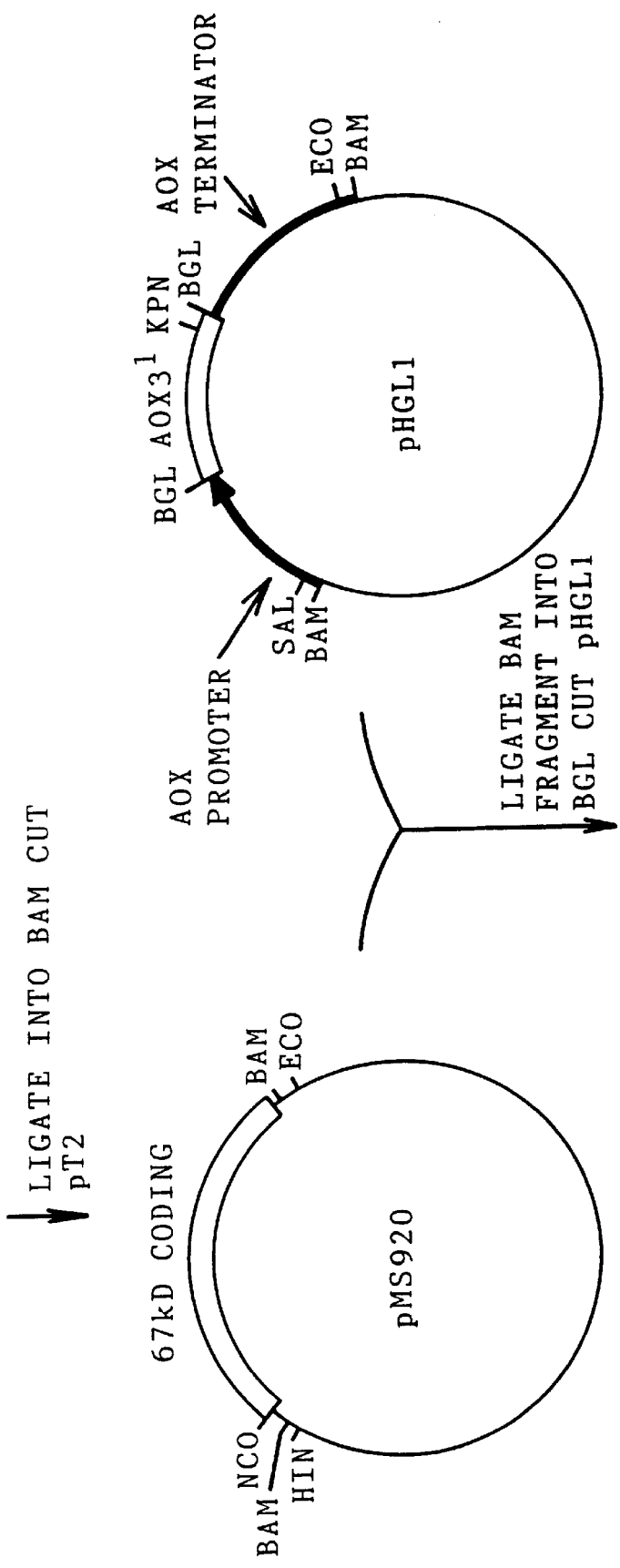
FIG. 11A

SEQUENCE LISTING ( 1 ) GENERAL INFORMATION:

( i i i ) NUMBER OF SEQUENCES: 28

( 2 ) INFORMATION FOR SEQ ID NO: 1:

( i ) SEQUENCE CHARACTERISTICS:
        ( A ) LENGTH: 1867 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Theobroma cacao ( i x ) FEATURE:
        ( A ) NAME/KEY: CDS
        ( B ) LOCATION: 14..1711

( x i ) SEQUENCE DESCRIPTION: SEQ ID NO: 1:

```
AAGCATAGCA  AAT  ATG  GTG  ATC  AGT  AAG  TCT  CCT  TTC  ATA  GTT  TTG  ATC              49
                Met  Val  Ile  Ser  Lys  Ser  Pro  Phe  Ile  Val  Leu  Ile
                 1                  5                           10

TTC  TCT  CTT  CTC  CTT  TCT  TTT  GCG  TTG  CTT  TGT  TCT  GGT  GTC  AGC  GCC           97
Phe  Ser  Leu  Leu  Leu  Ser  Phe  Ala  Leu  Leu  Cys  Ser  Gly  Val  Ser  Ala
          15                      20                  25

TAT  GGC  AGA  AAA  CAA  TAT  GAG  CGT  GAT  CCT  CGA  CAG  CAA  TAC  GAG  CAA          145
Tyr  Gly  Arg  Lys  Gln  Tyr  Glu  Arg  Asp  Pro  Arg  Gln  Gln  Tyr  Glu  Gln
     30                      35                       40

TGC  CAG  AGG  CGA  TGC  GAG  TCG  GAA  GCG  ACT  GAA  GAA  AGG  GAG  CAA  GAG          193
Cys  Gln  Arg  Arg  Cys  Glu  Ser  Glu  Ala  Thr  Glu  Glu  Arg  Glu  Gln  Glu
45                       50                       55                       60

CAG  TGT  GAA  CAA  CGC  TGT  GAA  AGG  GAG  TAC  AAG  GAG  CAG  CAG  AGA  CAG          241
Gln  Cys  Glu  Gln  Arg  Cys  Glu  Arg  Glu  Tyr  Lys  Glu  Gln  Gln  Arg  Gln
               65                        70                       75
```

| | | | | | | | | | | | | | | | | |
|---|---|---|---|---|---|---|---|---|---|---|---|---|---|---|---|---|
| CAA | GAA | GAA | GAG | CTT | CAA | AGG | CAA | TAC | CAG | CAA | TGT | CAA | GGG | CGT | TGT | 289 |
| Gln | Glu | Glu | Glu 80 | Leu | Gln | Arg | Gln | Tyr 85 | Gln | Gln | Cys | Gln | Gly 90 | Arg | Cys | |
| CAA | GAG | CAA | CAA | CAG | GGG | CAG | AGA | GAG | CAG | CAG | CAG | TGC | CAG | AGA | AAA | 337 |
| Gln | Glu | Gln | Gln 95 | Gln | Gly | Gln | Arg | Glu 100 | Gln | Gln | Gln | Cys 105 | Gln | Arg | Lys | |
| TGC | TGG | GAG | CAA | TAT | AAG | GAA | CAA | GAG | AGA | GGC | GAG | CAC | GAG | AAT | TAC | 385 |
| Cys | Trp 110 | Glu | Gln | Tyr | Lys 115 | Glu | Gln | Glu | Arg | Gly 120 | Glu | His | Glu | Asn | Tyr | |
| CAT | AAT | CAC | AAA | AAA | AAT | AGG | AGC | GAA | GAA | GAA | GAA | GGG | CAA | CAA | AGA | 433 |
| His 125 | Asn | His | Lys | Lys | Asn 130 | Arg | Ser | Glu | Glu | Glu 135 | Glu | Gly | Gln | Gln | Arg 140 | |
| AAC | AAT | CCT | TAC | TAT | TTT | CCT | AAA | AGA | AGA | TCA | TTC | CAA | ACT | CGA | TTC | 481 |
| Asn | Asn | Pro | Tyr | Tyr 145 | Phe | Pro | Lys | Arg | Arg 150 | Ser | Phe | Gln | Thr | Arg 155 | Phe | |
| AGG | GAT | GAA | GAG | GGC | AAC | TTC | AAG | ATC | CTC | CAG | AGG | TTT | GCT | GAG | AAC | 529 |
| Arg | Asp | Glu | Glu 160 | Gly | Asn | Phe | Lys | Ile 165 | Leu | Gln | Arg | Phe | Ala 170 | Glu | Asn | |
| TCT | CCT | CCA | CTC | AAG | GGC | ATC | AAC | GAT | TAC | CGC | TTG | GCC | ATG | TTC | GAA | 577 |
| Ser | Pro | Pro 175 | Leu | Lys | Gly | Ile | Asn 180 | Asp | Tyr | Arg | Leu | Ala 185 | Met | Phe | Glu | |
| GCA | AAT | CCC | AAC | ACT | TTT | ATT | CTT | CCG | CAC | CAC | TGT | GAT | GCT | GAG | GCA | 625 |
| Ala | Asn 190 | Pro | Asn | Thr | Phe | Ile 195 | Leu | Pro | His | His | Cys 200 | Asp | Ala | Glu | Ala | |
| ATT | TAC | TTC | GTG | ACA | AAC | GGA | AAG | GGG | ACA | ATT | ACG | TTT | GTG | ACT | CAT | 673 |
| Ile 205 | Tyr | Phe | Val | Thr | Asn 210 | Gly | Lys | Gly | Thr | Ile 215 | Thr | Phe | Val | Thr | His 220 | |
| GAA | AAC | AAA | GAG | TCC | TAT | AAT | GTA | CAG | CGT | GGA | ACA | GTA | GTC | AGC | GTT | 721 |
| Glu | Asn | Lys | Glu | Ser 225 | Tyr | Asn | Val | Gln | Arg 230 | Gly | Thr | Val | Val | Ser 235 | Val | |
| CCT | GCA | GGA | AGC | ACT | GTT | TAC | GTG | GTT | AGC | CAA | GAC | AAC | CAA | GAG | AAG | 769 |
| Pro | Ala | Gly | Ser 240 | Thr | Val | Tyr | Val | Val 245 | Ser | Gln | Asp | Asn | Gln 250 | Glu | Lys | |
| CTA | ACC | ATA | GCT | GTG | CTC | GCC | CTG | CCT | GTT | AAT | TCT | CCT | GGC | AAA | TAT | 817 |
| Leu | Thr | Ile 255 | Ala | Val | Leu | Ala | Leu 260 | Pro | Val | Asn | Ser | Pro 265 | Gly | Lys | Tyr | |
| GAG | TTA | TTC | TTC | CCC | GCT | GGA | AAT | AAT | AAA | CCT | GAA | TCA | TAT | TAC | GGA | 865 |
| Glu | Leu 270 | Phe | Phe | Pro | Ala | Gly 275 | Asn | Asn | Lys | Pro | Glu 280 | Ser | Tyr | Tyr | Gly | |
| GCC | TTC | AGC | TAT | GAA | GTT | CTT | GAG | ACC | GTC | TTC | AAT | ACA | CAA | AGA | GAG | 913 |
| Ala | Phe 285 | Ser | Tyr | Glu | Val | Leu 290 | Glu | Thr | Val | Phe | Asn 295 | Thr | Gln | Arg | Glu 300 | |
| AAG | CTG | GAG | GAG | ATC | TTG | GAG | GAA | CAG | AGA | GGG | CAG | AAG | AGG | CAG | CAG | 961 |
| Lys | Leu | Glu | Glu | Ile 305 | Leu | Glu | Glu | Gln | Arg 310 | Gly | Gln | Lys | Arg | Gln 315 | Gln | |
| GGG | CAG | CAG | GGT | ATG | TTC | CGG | AAA | GCC | AAA | CCA | GAG | CAG | ATA | AGA | GCA | 1009 |
| Gly | Gln | Gln | Gly 320 | Met | Phe | Arg | Lys | Ala 325 | Lys | Pro | Glu | Gln | Ile 330 | Arg | Ala | |
| ATA | AGC | CAA | CAA | GCT | ACT | TCT | CCA | AGG | CAC | AGA | GGC | GGG | GAG | AGA | CTT | 1057 |
| Ile | Ser | Gln 335 | Gln | Ala | Thr | Ser | Pro 340 | Arg | His | Arg | Gly | Gly 345 | Glu | Arg | Leu | |
| GCC | ATC | AAT | CTA | TTG | AGC | CAA | TCG | CCT | GTC | TAC | TCC | AAC | CAA | AAC | GGA | 1105 |
| Ala | Ile | Asn | Leu 350 | Leu | Ser | Gln | Ser | Pro 355 | Val | Tyr | Ser | Asn | Gln 360 | Asn | Gly | |
| CGC | TTC | TTT | GAG | GCT | TGT | CCT | GAG | GAC | TTC | AGT | CAA | TTT | CAG | AAC | ATG | 1153 |
| Arg | Phe 365 | Phe | Glu | Ala | Cys | Pro 370 | Glu | Asp | Phe | Ser | Gln 375 | Phe | Gln | Asn | Met 380 | |
| GAT | GTC | GCT | GTT | TCA | GCC | TTC | AAA | CTG | AAT | CAG | GGA | GCC | ATA | TTT | GTG | 1201 |
| Asp | Val | Ala | Val | Ser 385 | Ala | Phe | Lys | Leu | Asn 390 | Gln | Gly | Ala | Ile | Phe 395 | Val | |

| | | | | | | | | | | | | | | | | |
|---|---|---|---|---|---|---|---|---|---|---|---|---|---|---|---|---|
| CCA | CAC | TAC | AAT | TCT | AAG | GCT | ACA | TTC | GTG | GTG | TTT | GTC | ACG | GAC | GGA | 1249 |
| Pro | His | Tyr | Asn | Ser | Lys | Ala | Thr | Phe | Val | Val | Phe | Val | Thr | Asp | Gly | |
| | | | 400 | | | | 405 | | | | | 410 | | | | |
| TAT | GGG | TAC | GCT | CAA | ATG | GCT | TGC | CCG | CAT | CTC | TCC | AGA | CAG | AGC | CAG | 1297 |
| Tyr | Gly | Tyr | Ala | Gln | Met | Ala | Cys | Pro | His | Leu | Ser | Arg | Gln | Ser | Gln | |
| | | 415 | | | | | 420 | | | | | 425 | | | | |
| GGA | TCC | CAA | AGT | GGA | AGG | CAA | GAC | AGA | AGA | GAA | CAA | GAA | GAA | GAG | TCA | 1345 |
| Gly | Ser | Gln | Ser | Gly | Arg | Gln | Asp | Arg | Arg | Glu | Gln | Glu | Glu | Glu | Ser | |
| | | 430 | | | | 435 | | | | | 440 | | | | | |
| GAA | GAG | GAG | ACA | TTT | GGA | GAA | TTC | CAG | CAG | GTC | AAA | GCC | CCA | TTG | TCA | 1393 |
| Glu | Glu | Glu | Thr | Phe | Gly | Glu | Phe | Gln | Gln | Val | Lys | Ala | Pro | Leu | Ser | |
| 445 | | | | | 450 | | | | | 455 | | | | | 460 | |
| CCT | GGT | GAC | GTC | TTT | GTA | GCC | CCG | GCA | GGC | CAT | GCA | GTT | ACA | TTC | TTT | 1441 |
| Pro | Gly | Asp | Val | Phe | Val | Ala | Pro | Ala | Gly | His | Ala | Val | Thr | Phe | Phe | |
| | | | | 465 | | | | | 470 | | | | | 475 | | |
| GCA | TCC | AAA | GAC | CAG | CCC | CTG | AAT | GCA | GTT | GCG | TTT | GGA | CTC | AAC | GCC | 1489 |
| Ala | Ser | Lys | Asp | Gln | Pro | Leu | Asn | Ala | Val | Ala | Phe | Gly | Leu | Asn | Ala | |
| | | | 480 | | | | | 485 | | | | | 490 | | | |
| CAG | AAC | AAC | CAG | AGA | ATT | TTC | CTT | GCA | GGG | AAA | AAG | AAC | TTG | GTC | AGA | 1537 |
| Gln | Asn | Asn | Gln | Arg | Ile | Phe | Leu | Ala | Gly | Lys | Lys | Asn | Leu | Val | Arg | |
| | | 495 | | | | | 500 | | | | | 505 | | | | |
| CAA | ATG | GAT | AGC | GAG | GCA | AAG | GAG | TTA | TCA | TTT | GGG | GTA | CCA | TCG | AAA | 1585 |
| Gln | Met | Asp | Ser | Glu | Ala | Lys | Glu | Leu | Ser | Phe | Gly | Val | Pro | Ser | Lys | |
| | 510 | | | | | 515 | | | | | 520 | | | | | |
| TTG | GTA | GAT | AAT | ATA | TTC | AAC | AAC | CCG | GAT | GAG | TCG | TAT | TTC | ATG | TCT | 1633 |
| Leu | Val | Asp | Asn | Ile | Phe | Asn | Asn | Pro | Asp | Glu | Ser | Tyr | Phe | Met | Ser | |
| 525 | | | | | 530 | | | | | 535 | | | | | 540 | |
| TTC | TCT | CAA | CAG | AGG | CAG | CGT | CGA | GAT | GAA | AGG | AGG | GGC | AAT | CCC | TTG | 1681 |
| Phe | Ser | Gln | Gln | Arg | Gln | Arg | Arg | Asp | Glu | Arg | Arg | Gly | Asn | Pro | Leu | |
| | | | | 545 | | | | | 550 | | | | | 555 | | |
| GCC | TCA | ATT | CTG | GAC | TTT | GCC | CGC | TTG | TTC | TAAGCAGCTG | CTTCCACTTT | | | | | 1731 |
| Ala | Ser | Ile | Leu | Asp | Phe | Ala | Arg | Leu | Phe | | | | | | | |
| | | | 560 | | | | | 565 | | | | | | | | |

TGTATCAGAC ATGCAGAGGC ATGTAATGCA ATAAATAAGT TGGCCTATGT AAAGAGGAGA 1791

GAGTTTGCTT TTGTCTTGTT CTAACCTTGT TTTGAACTAG TAAACTTTCA ATGTAATGAG 1851

AGTTGTTATC TTTCTA 1867

(2) INFORMATION FOR SEQ ID NO: 2:

(i) SEQUENCE CHARACTERISTICS:
        (A) LENGTH: 566 amino acids
        (B) TYPE: amino acid
        (D) TOPOLOGY: linear (ii) MOLECULE TYPE: protein (xi) SEQUENCE DESCRIPTION: SEQ ID NO: 2:

| | | | | | | | | | | | | | | | |
|---|---|---|---|---|---|---|---|---|---|---|---|---|---|---|---|
| Met | Val | Ile | Ser | Lys | Ser | Pro | Phe | Ile | Val | Leu | Ile | Phe | Ser | Leu | Leu |
| 1 | | | | 5 | | | | | 10 | | | | | 15 | |
| Leu | Ser | Phe | Ala | Leu | Leu | Cys | Ser | Gly | Val | Ser | Ala | Tyr | Gly | Arg | Lys |
| | | | 20 | | | | | 25 | | | | | 30 | | |
| Gln | Tyr | Glu | Arg | Asp | Pro | Arg | Gln | Gln | Tyr | Glu | Gln | Cys | Gln | Arg | Arg |
| | | 35 | | | | | 40 | | | | | 45 | | | |
| Cys | Glu | Ser | Glu | Ala | Thr | Glu | Glu | Arg | Glu | Gln | Glu | Gln | Cys | Glu | Gln |
| | 50 | | | | | 55 | | | | | 60 | | | | |
| Arg | Cys | Glu | Arg | Glu | Tyr | Lys | Glu | Gln | Gln | Arg | Gln | Glu | Glu | Glu | Glu |
| 65 | | | | | 70 | | | | | 75 | | | | | 80 |
| Leu | Gln | Arg | Gln | Tyr | Gln | Gln | Cys | Gln | Gly | Arg | Cys | Gln | Glu | Gln | Gln |
| | | | | 85 | | | | | 90 | | | | | 95 | |

Gln Gly Gln Arg Glu Gln Gln Gln Cys Gln Arg Lys Cys Trp Glu Gln
                100                 105                 110

Tyr Lys Glu Gln Glu Arg Gly Glu His Glu Asn Tyr Asn His Lys
        115                 120                 125

Lys Asn Arg Ser Glu Glu Glu Gly Gln Gln Arg Asn Asn Pro Tyr
    130                 135                 140

Tyr Phe Pro Lys Arg Arg Ser Phe Gln Thr Arg Phe Arg Asp Glu Glu
145                 150                 155                 160

Gly Asn Phe Lys Ile Leu Gln Arg Phe Ala Glu Asn Ser Pro Pro Leu
                165                 170                 175

Lys Gly Ile Asn Asp Tyr Arg Leu Ala Met Phe Glu Ala Asn Pro Asn
            180                 185                 190

Thr Phe Ile Leu Pro His His Cys Asp Ala Glu Ala Ile Tyr Phe Val
        195                 200                 205

Thr Asn Gly Lys Gly Thr Ile Thr Phe Val Thr His Glu Asn Lys Glu
    210                 215                 220

Ser Tyr Asn Val Gln Arg Gly Thr Val Val Ser Val Pro Ala Gly Ser
225                 230                 235                 240

Thr Val Tyr Val Val Ser Gln Asp Asn Gln Glu Lys Leu Thr Ile Ala
                245                 250                 255

Val Leu Ala Leu Pro Val Asn Ser Pro Gly Lys Tyr Glu Leu Phe Phe
            260                 265                 270

Pro Ala Gly Asn Asn Lys Pro Glu Ser Tyr Tyr Gly Ala Phe Ser Tyr
        275                 280                 285

Glu Val Leu Glu Thr Val Phe Asn Thr Gln Arg Glu Lys Leu Glu Glu
    290                 295                 300

Ile Leu Glu Glu Gln Arg Gly Gln Lys Arg Gln Gln Gly Gln Gln Gly
305                 310                 315                 320

Met Phe Arg Lys Ala Lys Pro Glu Gln Ile Arg Ala Ile Ser Gln Gln
                325                 330                 335

Ala Thr Ser Pro Arg His Arg Gly Gly Glu Arg Leu Ala Ile Asn Leu
            340                 345                 350

Leu Ser Gln Ser Pro Val Tyr Ser Asn Gln Asn Gly Arg Phe Phe Glu
        355                 360                 365

Ala Cys Pro Glu Asp Phe Ser Gln Phe Gln Asn Met Asp Val Ala Val
    370                 375                 380

Ser Ala Phe Lys Leu Asn Gln Gly Ala Ile Phe Val Pro His Tyr Asn
385                 390                 395                 400

Ser Lys Ala Thr Phe Val Val Phe Val Thr Asp Gly Tyr Gly Tyr Ala
                405                 410                 415

Gln Met Ala Cys Pro His Leu Ser Arg Gln Ser Gln Gly Ser Gln Ser
            420                 425                 430

Gly Arg Gln Asp Arg Arg Glu Gln Glu Glu Glu Ser Glu Glu Glu Thr
        435                 440                 445

Phe Gly Glu Phe Gln Gln Val Lys Ala Pro Leu Ser Pro Gly Asp Val
450                 455                 460

Phe Val Ala Pro Ala Gly His Ala Val Thr Phe Phe Ala Ser Lys Asp
465                 470                 475                 480

Gln Pro Leu Asn Ala Val Ala Phe Gly Leu Asn Ala Gln Asn Asn Gln
                485                 490                 495

Arg Ile Phe Leu Ala Gly Lys Lys Asn Leu Val Arg Gln Met Asp Ser
            500                 505                 510

Glu Ala Lys Glu Leu Ser Phe Gly Val Pro Ser Lys Leu Val Asp Asn
        515                 520                 525

```
Ile  Phe  Asn  Asn  Pro  Asp  Glu  Ser  Tyr  Phe  Met  Ser  Phe  Ser  Gln  Gln
          530                 535                      540

Arg  Gln  Arg  Arg  Asp  Glu  Arg  Arg  Gly  Asn  Pro  Leu  Ala  Ser  Ile  Leu
545                      550                 555                           560

Asp  Phe  Ala  Arg  Leu  Phe
                    565
```

( 2 ) INFORMATION FOR SEQ ID NO: 3:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Theobroma cacao ( i x ) FEATURE:
        ( A ) NAME/KEY: Region
        ( B ) LOCATION: 1..14
        ( D ) OTHER INFORMATION: /note= "Tentative N-terminal
            sequence of 47kD mature protein"

( x i ) SEQUENCE DESCRIPTION: SEQ ID NO: 3:

```
Glu  Glu  Pro  Gly  Ser  Gln  Phe  Ala  Asn  Pro  Ala  Tyr  His  Phe
1                   5                        10
```

( 2 ) INFORMATION FOR SEQ ID NO: 4:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: YEAST PYRUVATE KINASE GENE ( i x ) FEATURE:
        ( A ) NAME/KEY: CDS
        ( B ) LOCATION: 41

( x i ) SEQUENCE DESCRIPTION: SEQ ID NO: 4:

```
TTTACAAGAC  ACCAATCAAA  ACAAATAAAA  CATCATCACA  ATG  TCT  AGA           49
                                                Met  Ser  Arg
```

( 2 ) INFORMATION FOR SEQ ID NO: 5:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 5:

```
Met  Ser  Arg
1
```

( 2 ) INFORMATION FOR SEQ ID NO: 6:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear (i i) MOLECULE TYPE: DNA (v i) ORIGINAL SOURCE:
    (A) ORGANISM: YEAST PYRUVATE KINASE GENE (i x) FEATURE:
    (A) NAME/KEY: mutation
    (B) LOCATION: 6..11
    (D) OTHER INFORMATION: /note= "Hin cloning site introduced"

(i x) FEATURE:
    (A) NAME/KEY: CDS
    (B) LOCATION: 41

(x i) SEQUENCE DESCRIPTION: SEQ ID NO: 6:

```
TTTACAAGCT TCCAATCAAA ACAAATAAAA CATCATCACA ATG TCT AGA              49
                                            Met Ser Arg
```

(2) INFORMATION FOR SEQ ID NO: 7:

(i) SEQUENCE CHARACTERISTICS:
        (A) LENGTH: 3 amino acids
        (B) TYPE: amino acid
        (D) TOPOLOGY: linear (i i) MOLECULE TYPE: protein (x i) SEQUENCE DESCRIPTION: SEQ ID NO: 7:

```
Met Ser Arg
 1
```

(2) INFORMATION FOR SEQ ID NO: 8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (i i) MOLECULE TYPE: DNA (i x) FEATURE:
        (A) NAME/KEY: misc_feature
        (B) LOCATION: 1..33
        (D) OTHER INFORMATION: /product="Hin-Nco linker"

(x i) SEQUENCE DESCRIPTION: SEQ ID NO: 8:

```
AGCTTCCAAT CAAAACAAAT AAAACATCAT CAC                                 33
```

(2) INFORMATION FOR SEQ ID NO: 9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (i i) MOLECULE TYPE: DNA (i x) FEATURE:
        (A) NAME/KEY: misc_feature
        (B) LOCATION: 1..33
        (D) OTHER INFORMATION: /product="Hin-Nco linker"

(x i) SEQUENCE DESCRIPTION: SEQ ID NO: 9:

```
CATGGTGATG ATGTTTTATT TGTTTTGATT GGA                                 33
```

(2) INFORMATION FOR SEQ ID NO: 10:

(i) SEQUENCE CHARACTERISTICS:

(A) LENGTH: 49 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: CDS
(B) LOCATION: 41
(D) OTHER INFORMATION: /product="67kD expression vector A"

(xi) SEQUENCE DESCRIPTION: SEQ ID NO: 10:

```
TTTACAAGCT TCCAATCAAA ACAAATAAAA CATCATCACC ATG GTG ATC      49
                                            Met Val Ile
```

(2) INFORMATION FOR SEQ ID NO: 11:

(i) SEQUENCE CHARACTERISTICS:
(A) LENGTH: 3 amino acids
(B) TYPE: amino acid
(D) TOPOLOGY: linear (ii) MOLECULE TYPE: protein (xi) SEQUENCE DESCRIPTION: SEQ ID NO: 11:

```
Met Val Ile
 1
```

(2) INFORMATION FOR SEQ ID NO: 12:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(A) ORGANISM: YEAST ALPHA-FACTOR SIGNAL SEQUENCE (ix) FEATURE:
(A) NAME/KEY: CDS
(B) LOCATION: 1..27

(xi) SEQUENCE DESCRIPTION: SEQ ID NO: 12:

```
GAA GGG GTA AGC TTG GAT AAA AGA GAG                          27
Glu Gly Val Ser Leu Asp Lys Arg Glu
 1               5
```

(2) INFORMATION FOR SEQ ID NO: 13:

(i) SEQUENCE CHARACTERISTICS:
(A) LENGTH: 9 amino acids
(B) TYPE: amino acid
(D) TOPOLOGY: linear (ii) MOLECULE TYPE: protein (xi) SEQUENCE DESCRIPTION: SEQ ID NO: 13:

```
Glu Gly Val Ser Leu Asp Lys Arg Glu
 1               5
```

(2) INFORMATION FOR SEQ ID NO: 14:

(i) SEQUENCE CHARACTERISTICS:
(A) LENGTH: 17 base pairs
(B) TYPE: nucleic acid
(C) STRANDEDNESS: single
(D) TOPOLOGY: linear (  i i  ) MOLECULE TYPE: DNA (  i x  ) FEATURE:
    ( A ) NAME/KEY: misc_feature
    ( B ) LOCATION: 1..17
    ( D ) OTHER INFORMATION: /product="Hin-Nco linker"

(  x i  ) SEQUENCE DESCRIPTION: SEQ ID NO: 14:

AGCTTGGATA AAAGAGC    17

( 2 ) INFORMATION FOR SEQ ID NO: 15:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: misc_feature
        ( B ) LOCATION: 1..17
        ( D ) OTHER INFORMATION: /product="Hin-Nco linker"

( x i ) SEQUENCE DESCRIPTION: SEQ ID NO: 15:

CATGGCTCTT TTATCCA    17

( 2 ) INFORMATION FOR SEQ ID NO: 16:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: CDS
        ( B ) LOCATION: 1..36
        ( D ) OTHER INFORMATION: /product="In phase fusion of 67kD
            coding region"

( x i ) SEQUENCE DESCRIPTION: SEQ ID NO: 16:

GAA GGG GTA AGC TTG GAT AAA AGA GCC ATG GCG TTG    36
Glu Gly Val Ser Leu Asp Lys Arg Ala Met Ala Leu
1            5                  10

( 2 ) INFORMATION FOR SEQ ID NO: 17:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 17:

Glu Gly Val Ser Leu Asp Lys Arg Ala Met Ala Leu
1            5                  10

( 2 ) INFORMATION FOR SEQ ID NO: 18:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein (ix) FEATURE:
    (A) NAME/KEY: CDS
    (B) LOCATION: 1..9
    (D) OTHER INFORMATION: /product="Cyanogen bromide peptide"

(xi) SEQUENCE DESCRIPTION: SEQ ID NO: 18:

Met  Phe  Glu  Ala  Asn  Pro  Asn  Thr  Phe
   1                       5

(2) INFORMATION FOR SEQ ID NO: 19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: misc_feature
        (B) LOCATION: 1..17
        (D) OTHER INFORMATION: /product="N at position 6 = T or C
            N at position 9 = A or G
            N at position 12 = T,C,A or G
            N at position 15 = T or C"

(xi) SEQUENCE DESCRIPTION: SEQ ID NO: 19:

ATG TTN GAN GCN AAN CC                                        17

(2) INFORMATION FOR SEQ ID NO: 20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 20:

TAGCAACCAT GGTGATCA                                             18

(2) INFORMATION FOR SEQ ID NO: 21:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 21:

AGCATAGCAA CCATGGTTGC TTTGTTCT                               28

(2) INFORMATION FOR SEQ ID NO: 22:

(i) SEQUENCE CHARACTERISTICS:
        (A) LENGTH: 566 amino acids
        (B) TYPE: amino acid
        (D) TOPOLOGY: linear (ii) MOLECULE TYPE: protein (vi) ORIGINAL SOURCE:
        (A) ORGANISM: Theobroma cacao (ix) FEATURE:
        (A) NAME/KEY: Protein
        (B) LOCATION: 1..566
        (D) OTHER INFORMATION: /note= "67 kD Precursor Protein"

( x i ) SEQUENCE DESCRIPTION: SEQ ID NO: 22:

| Met | Val | Ile | Ser | Lys | Ser | Pro | Phe | Ile | Val | Leu | Ile | Phe | Ser | Leu |
|---|---|---|---|---|---|---|---|---|---|---|---|---|---|---|
| 1 | | | | 5 | | | | | 10 | | | | | 15 |

| Leu | Ser | Phe | Ala | Leu | Leu | Cys | Ser | Gly | Val | Ser | Ala | Tyr | Gly | Arg | Lys |
|---|---|---|---|---|---|---|---|---|---|---|---|---|---|---|---|
| | | | 20 | | | | 25 | | | | | 30 | | | |

Gln Tyr Glu Arg Asp Pro Arg Gln Gln Tyr Glu Gln Cys Gln Arg Arg
         35               40               45

Cys Glu Ser Glu Ala Thr Glu Glu Arg Glu Gln Glu Gln Cys Glu Gln
    50               55                       60

Arg Cys Glu Arg Glu Tyr Lys Glu Gln Gln Arg Gln Gln Glu Glu Glu
65                   70                   75                   80

Leu Gln Arg Gln Tyr Gln Gln Cys Gln Gly Arg Cys Gln Glu Gln Gln
                 85                   90                   95

Gln Gly Gln Arg Glu Gln Gln Gln Cys Gln Arg Lys Cys Trp Glu Gln
             100                 105                 110

Tyr Lys Glu Gln Glu Arg Gly Glu His Glu Asn Tyr His Asn His Lys
         115                 120                 125

Lys Asn Arg Ser Glu Glu Glu Glu Gly Gln Gln Arg Asn Asn Pro Tyr
    130                 135                 140

Tyr Phe Pro Lys Arg Arg Ser Phe Gln Thr Arg Phe Arg Asp Glu Glu
145                 150                 155                 160

Gly Asn Phe Lys Ile Leu Gln Arg Phe Ala Glu Asn Ser Pro Pro Leu
                 165                 170                 175

Lys Gly Ile Asn Asp Tyr Arg Leu Ala Met Phe Glu Ala Asn Pro Asn
             180                 185                 190

Thr Phe Ile Leu Pro His His Cys Asp Ala Glu Ala Ile Tyr Phe Val
         195                 200                 205

Thr Asn Gly Lys Gly Thr Ile Thr Phe Val Thr His Glu Asn Lys Glu
    210                 215                 220

Ser Tyr Asn Val Gln Arg Gly Thr Val Val Ser Val Pro Ala Gly Ser
225                 230                 235                 240

Thr Val Tyr Val Val Ser Gln Asp Asn Gln Glu Lys Leu Thr Ile Ala
                 245                 250                 255

Val Leu Ala Leu Pro Val Asn Ser Pro Gly Lys Tyr Glu Leu Phe Phe
             260                 265                 270

Pro Ala Gly Asn Asn Lys Pro Glu Ser Tyr Tyr Gly Ala Phe Ser Tyr
         275                 280                 285

Glu Val Leu Glu Thr Val Phe Asn Thr Gln Arg Glu Lys Leu Glu Glu
    290                 295                 300

Ile Leu Glu Glu Gln Arg Gly Gln Lys Arg Gln Gln Gly Gln Gln Gly
305                 310                 315                 320

Met Phe Arg Lys Ala Lys Pro Glu Gln Ile Arg Ala Ile Ser Gln Gln
                 325                 330                 335

Ala Thr Ser Pro Arg His Arg Gly Gly Glu Arg Leu Ala Ile Asn Leu
             340                 345                 350

Leu Ser Gln Ser Pro Val Tyr Ser Asn Gln Asn Gly Arg Phe Phe Glu
         355                 360                 365

Ala Cys Pro Glu Asp Phe Ser Gln Phe Gln Asn Met Asp Val Ala Val
    370                 375                 380

Ser Ala Phe Lys Leu Asn Gln Gly Ala Ile Phe Val Pro His Tyr Asn
385                 390                 395                 400

Ser Lys Ala Thr Phe Val Val Phe Val Thr Asp Gly Tyr Gly Tyr Ala
                 405                 410                 415

| Gln | Met | Ala | Cys | Pro | His | Leu | Ser | Arg | Gln | Ser | Gln | Gly | Ser | Gln | Ser |
| | | | 420 | | | | 425 | | | | 430 | | | | |

| Gly | Arg | Gln | Asp | Arg | Arg | Glu | Gln | Glu | Glu | Ser | Glu | Glu | Thr |
| | | 435 | | | | 440 | | | | 445 | | | |

| Phe | Gly | Glu | Phe | Gln | Gln | Val | Lys | Ala | Pro | Leu | Ser | Pro | Gly | Asp | Val |
| | 450 | | | | 455 | | | | | 460 | | | | | |

| Phe | Val | Ala | Pro | Ala | Gly | His | Ala | Val | Thr | Phe | Phe | Ala | Ser | Lys | Asp |
| 465 | | | | 470 | | | | | 475 | | | | | | 480 |

| Gln | Pro | Leu | Asn | Ala | Val | Ala | Phe | Gly | Leu | Asn | Ala | Gln | Asn | Asn | Gln |
| | | | | 485 | | | | | 490 | | | | | 495 | |

| Arg | Ile | Phe | Leu | Ala | Gly | Lys | Lys | Asn | Leu | Val | Arg | Gln | Met | Asp | Ser |
| | | | 500 | | | | | 505 | | | | | 510 | | |

| Glu | Ala | Lys | Glu | Leu | Ser | Phe | Gly | Val | Pro | Ser | Lys | Leu | Val | Asp | Asn |
| | | 515 | | | | | 520 | | | | | 525 | | | |

| Ile | Phe | Asn | Asn | Pro | Asp | Glu | Ser | Tyr | Phe | Met | Ser | Phe | Ser | Gln | Gln |
| | 530 | | | | | 535 | | | | | 540 | | | | |

| Arg | Gln | Arg | Arg | Asp | Glu | Arg | Arg | Gly | Asn | Pro | Leu | Ala | Ser | Ile | Leu |
| 545 | | | | | 550 | | | | | 555 | | | | | 560 |

| Asp | Phe | Ala | Arg | Leu | Phe |
| | | | | 565 | |

(2) INFORMATION FOR SEQ ID NO: 23:

(i) SEQUENCE CHARACTERISTICS:
        (A) LENGTH: 587 amino acids
        (B) TYPE: amino acid
        (D) TOPOLOGY: linear (ii) MOLECULE TYPE: protein (vi) ORIGINAL SOURCE:
        (A) ORGANISM: Gossypium hirsutum (ix) FEATURE:
        (A) NAME/KEY: Protein
        (B) LOCATION: 1..587
        (D) OTHER INFORMATION: /note= "Vicilin from G. hirsutum"

(xi) SEQUENCE DESCRIPTION: SEQ ID NO: 23:

| Met | Val | Arg | Asn | Lys | Ser | Ala | Cys | Val | Val | Leu | Leu | Phe | Ser | Leu | Phe |
| 1 | | | | 5 | | | | | 10 | | | | | 15 | |

| Leu | Ser | Phe | Gly | Leu | Leu | Cys | Ser | Ala | Lys | Asp | Phe | Pro | Gly | Arg | Arg |
| | | | 20 | | | | | 25 | | | | | 30 | | |

| Gly | Asp | Asp | Asp | Pro | Pro | Lys | Arg | Tyr | Glu | Asp | Cys | Arg | Arg | Arg | Cys |
| | | 35 | | | | | 40 | | | | | 45 | | | |

| Glu | Trp | Asp | Thr | Arg | Gly | Gln | Lys | Glu | Gln | Gln | Gln | Cys | Glu | Glu | Ser |
| | 50 | | | | | 55 | | | | | 60 | | | | |

| Cys | Lys | Ser | Gln | Tyr | Gly | Glu | Lys | Asp | Gln | Gln | Arg | His | Arg | Pro | Glu |
| 65 | | | | | 70 | | | | | 75 | | | | | 80 |

| Asp | Pro | Gln | Arg | Arg | Tyr | Glu | Glu | Cys | Gln | Glu | Glu | Cys | Arg | Gln | Gln |
| | | | | 85 | | | | | 90 | | | | | 95 | |

| Glu | Glu | Arg | Gln | Arg | Pro | Gln | Cys | Gln | Gln | Arg | Cys | Ile | Lys | Arg | Phe |
| | | | 100 | | | | | 105 | | | | | 110 | | |

| Glu | Gln | Gln | Gln | Gln | Gln | Ser | Gln | Arg | Gln | Phe | Gln | Glu | Cys | Gln | Gln |
| | | | | 115 | | | | | 120 | | | | | 125 | |

| His | Cys | His | Gln | Gln | Glu | Gln | Arg | Pro | Glu | Arg | Lys | Gln | Gln | Cys | Val |
| | | 130 | | | | | 135 | | | | | 140 | | | |

| Ala | Glu | Cys | Arg | Glu | Arg | Tyr | Gln | Glu | Asn | Pro | Trp | Arg | Arg | Glu | Arg |
| 145 | | | | | 150 | | | | | 155 | | | | | 160 |

```
Glu  Glu  Glu  Ala  Glu  Glu  Glu  Thr  Glu  Glu  Gly  Glu  Gln  Glu  Gln
               165                 170                      175

Ser  His  Asn  Pro  Phe  His  Phe  His  Arg  Arg  Ser  Phe  Gln  Ser  Arg  Phe
               180                 185                      190

Arg  Glu  Glu  His  Gly  Asn  Phe  Arg  Val  Leu  Gln  Arg  Phe  Ala  Ser  Arg
          195                 200                      205

His  Pro  Ile  Leu  Arg  Gly  Ile  Asn  Glu  Phe  Arg  Leu  Ser  Ile  Leu  Glu
     210                      215                      220

Ala  Asn  Pro  Asn  Thr  Glu  Val  Leu  Pro  His  His  Cys  Asp  Ala  Glu  Lys
225                      230                 235                           240

Ile  Tyr  Leu  Val  Thr  Asn  Gly  Arg  Gly  Thr  Leu  Thr  Phe  Leu  Thr  His
               245                      250                           255

Glu  Asn  Lys  Glu  Ser  Tyr  Asn  Val  Val  Pro  Gly  Val  Val  Arg  Val
               260                 265                      270

Pro  Ala  Gly  Ser  Thr  Val  Tyr  Leu  Ala  Asn  Gln  Asp  Asn  Lys  Glu  Lys
               275                 280                      285

Leu  Ile  Ile  Ala  Val  Leu  His  Arg  Pro  Val  Asn  Asn  Pro  Arg  Gln  Phe
     290                 295                      300

Glu  Glu  Phe  Phe  Pro  Ala  Gly  Ser  Gln  Arg  Pro  Gln  Ser  Tyr  Leu  Arg
305                      310                 315                           320

Ala  Phe  Ser  Arg  Glu  Ile  Leu  Glu  Pro  Ala  Phe  Asn  Thr  Arg  Ser  Glu
               325                 330                      335

Gln  Leu  Asp  Glu  Leu  Phe  Gly  Gly  Arg  Gln  Ser  His  Arg  Arg  Gln  Gln
               340                 345                      350

Gly  Gln  Gly  Met  Phe  Arg  Lys  Ala  Ser  Gln  Glu  Gln  Ile  Arg  Ala  Leu
               355                 360                      365

Ser  Gln  Glu  Ala  Thr  Ser  Pro  Arg  Glu  Lys  Ser  Gly  Glu  Arg  Phe  Ala
          370                 375                      380

Phe  Asn  Leu  Leu  Tyr  Arg  Thr  Pro  Arg  Tyr  Ser  Asn  Gln  Asn  Gly  Arg
385                      390                 395                           400

Phe  Tyr  Glu  Ala  Cys  Pro  Arg  Glu  Phe  Arg  Gln  Leu  Ser  Asp  Ile  Asn
               405                 410                      415

Val  Thr  Val  Ser  Ala  Leu  Gln  Leu  Asn  Gln  Gly  Ser  Ile  Phe  Val  Pro
               420                 425                      430

His  Tyr  Asn  Ser  Lys  Ala  Thr  Phe  Val  Val  Leu  Val  Asn  Glu  Gly  Asn
               435                 440                      445

Gly  Tyr  Val  Glu  Met  Val  Ser  Pro  His  Leu  Pro  Arg  Gln  Ser  Ser  Phe
     450                      455                 460

Glu  Glu  Glu  Glu  Glu  Gln  Gln  Gln  Glu  Gln  Glu  Gln  Glu  Glu  Glu  Arg
465                      470                 475                           480

Arg  Ser  Gly  Gln  Tyr  Arg  Lys  Ile  Arg  Ser  Gln  Leu  Ser  Arg  Gly  Asp
               485                 490                      495

Ile  Phe  Val  Val  Pro  Ala  Asn  Phe  Pro  Val  Thr  Phe  Val  Ala  Ser  Gln
               500                 505                      510

Asn  Gln  Asn  Leu  Arg  Met  Thr  Gly  Phe  Gly  Leu  Tyr  Asn  Gln  Asn  Ile
          515                 520                      525

Asn  Pro  Asp  His  Asn  Gln  Arg  Ile  Phe  Val  Ala  Gly  Lys  Ile  Asn  His
     530                 535                      540

Val  Arg  Gln  Trp  Asp  Ser  Gln  Ala  Lys  Glu  Leu  Ala  Phe  Gly  Val  Ser
545                      550                      555                      560

Ser  Arg  Leu  Val  Asp  Glu  Ile  Phe  Asn  Asn  Pro  Gln  Glu  Ser  Tyr
               565                 570                      575

Phe  Val  Ser  Arg  Gln  Arg  Gln  Arg  Ala  Ser  Glu
```

580                         585

( 2 ) INFORMATION FOR SEQ ID NO: 24:

( i ) SEQUENCE CHARACTERISTICS:
            ( A ) LENGTH: 605 amino acids
            ( B ) TYPE: amino acid
            ( D ) TOPOLOGY: linear ( i i ) MOLECULE TYPE: protein ( v i ) ORIGINAL SOURCE:
            ( A ) ORGANISM: Glycine max ( i x ) FEATURE:
            ( A ) NAME/KEY: Protein
            ( B ) LOCATION: 1..605
            ( D ) OTHER INFORMATION: /note= "Vicilin from G. max"

( x i ) SEQUENCE DESCRIPTION: SEQ ID NO: 24:

| Met | Met | Arg | Ala | Arg | Phe | Pro | Leu | Leu | Leu | Leu | Gly | Leu | Val | Phe | Leu |
| 1 | | | | 5 | | | | | 10 | | | | | 15 | |
| Ala | Ser | Val | Ser | Val | Ser | Phe | Gly | Ile | Ala | Tyr | Trp | Glu | Lys | Glu | Asn |
| | | | 20 | | | | | 25 | | | | | 30 | | |
| Pro | Lys | His | Asn | Lys | Cys | Leu | Gln | Ser | Cys | Asn | Ser | Glu | Arg | Asp | Ser |
| | | | 35 | | | | | 40 | | | | | 45 | | |
| Tyr | Arg | Asn | Gln | Ala | Cys | His | Ala | Arg | Cys | Asn | Leu | Leu | Lys | Val | Glu |
| | | 50 | | | | | 55 | | | | | 60 | | | |
| Lys | Glu | Glu | Cys | Glu | Glu | Gly | Glu | Ile | Pro | Arg | Pro | Arg | Pro | Arg | Pro |
| 65 | | | | | 70 | | | | | 75 | | | | | 80 |
| Gln | His | Pro | Glu | Arg | Glu | Pro | Gln | Gln | Pro | Gly | Glu | Lys | Glu | Glu | Asp |
| | | | | 85 | | | | | 90 | | | | | 95 | |
| Glu | Asp | Glu | Gln | Pro | Arg | Pro | Ile | Pro | Phe | Pro | Arg | Pro | Gln | Pro | Arg |
| | | | | 100 | | | | | 105 | | | | | 110 | |
| Gln | Glu | Glu | Glu | His | Glu | Gln | Arg | Glu | Glu | Gln | Glu | Trp | Pro | Arg | Lys |
| | | | 115 | | | | | 120 | | | | | 125 | | |
| Glu | Glu | Lys | Arg | Gly | Glu | Lys | Gly | Ser | Glu | Glu | Glu | Asp | Glu | Asp | Glu |
| | 130 | | | | | 135 | | | | | 140 | | | | |
| Asp | Glu | Glu | Gln | Asp | Glu | Arg | Gln | Phe | Pro | Phe | Pro | Arg | Pro | Pro | His |
| 145 | | | | | 150 | | | | | 155 | | | | | 160 |
| Gln | Lys | Glu | Glu | Arg | Asn | Glu | Glu | Asp | Glu | Asp | Glu | Glu | Gln | Gln |
| | | | | 165 | | | | | 170 | | | | | 175 | |
| Arg | Glu | Ser | Glu | Glu | Ser | Glu | Asp | Ser | Glu | Leu | Arg | Arg | His | Lys | Asn |
| | | | | 180 | | | | | 185 | | | | | 190 | |
| Lys | Asn | Pro | Phe | Leu | Phe | Phe | Ser | Asn | Arg | Phe | Glu | Thr | Leu | Phe | Lys |
| | | | 195 | | | | | 200 | | | | | 205 | | |
| Asn | Gln | Tyr | Gly | Arg | Ile | Arg | Val | Leu | Gln | Arg | Phe | Asn | Gln | Arg | Ser |
| | | 210 | | | | | 215 | | | | | 220 | | | |
| Pro | Gln | Leu | Gln | Asn | Leu | Arg | Asp | Tyr | Arg | Ile | Leu | Glu | Phe | Asn | Ser |
| 225 | | | | | 230 | | | | | 235 | | | | | 240 |
| Lys | Pro | Asn | Thr | Leu | Leu | Leu | Pro | Asn | His | Ala | Asp | Ala | Asp | Tyr | Leu |
| | | | | 245 | | | | | 250 | | | | | 255 | |
| Ile | Val | Ile | Leu | Asn | Gly | Thr | Ala | Ile | Leu | Ser | Leu | Val | Asn | Asn | Asp |
| | | | 260 | | | | | 265 | | | | | 270 | | |
| Asp | Arg | Asp | Ser | Tyr | Arg | Leu | Gln | Ser | Gly | Asp | Ala | Leu | Arg | Val | Pro |
| | | | 275 | | | | | 280 | | | | | 285 | | |
| Ser | Gly | Thr | Thr | Tyr | Tyr | Val | Val | Asn | Pro | Asp | Asn | Asn | Glu | Asn | Leu |
| | | 290 | | | | | 295 | | | | | 300 | | | |
| Arg | Leu | Ile | Thr | Leu | Ala | Ile | Pro | Val | Asn | Lys | Pro | Gly | Arg | Phe | Glu |

|     |     |     |     | 305 |     |     |     |     | 310 |     |     |     |     | 315 |     |     |     |     | 320 |
| --- | --- | --- | --- | --- | --- | --- | --- | --- | --- | --- | --- | --- | --- | --- | --- | --- | --- | --- | --- |
| Ser | Phe | Phe | Leu | Ser | Ser | Thr | Glu | Ala | Gln | Gln | Ser | Tyr | Leu | Gln | Gly |
|     |     |     |     | 325 |     |     |     |     | 330 |     |     |     |     | 335 |     |
| Phe | Ser | Arg | Asn | Ile | Leu | Glu | Ala | Ser | Tyr | Asp | Thr | Lys | Phe | Glu | Glu |
|     |     |     | 340 |     |     |     |     | 345 |     |     |     |     | 350 |     |     |
| Ile | Asn | Lys | Val | Leu | Phe | Ser | Arg | Glu | Glu | Gly | Gln | Gln | Gln | Gly | Glu |
|     |     | 355 |     |     |     |     |     | 360 |     |     |     |     | 365 |     |     |
| Gln | Arg | Leu | Gln | Glu | Ser | Val | Ile | Val | Glu | Ile | Ser | Lys | Glu | Gln | Ile |
|     | 370 |     |     |     |     | 375 |     |     |     |     | 380 |     |     |     |     |
| Arg | Ala | Leu | Ser | Lys | Arg | Ala | Lys | Ser | Ser | Ser | Arg | Lys | Thr | Ile | Ser |
| 385 |     |     |     |     | 390 |     |     |     |     | 395 |     |     |     |     | 400 |
| Ser | Glu | Asp | Lys | Pro | Phe | Asn | Leu | Arg | Ser | Arg | Asp | Pro | Ile | Tyr | Ser |
|     |     |     |     | 405 |     |     |     |     | 410 |     |     |     |     | 415 |     |
| Asn | Lys | Leu | Gly | Lys | Phe | Phe | Glu | Ile | Thr | Pro | Glu | Lys | Asn | Pro | Gln |
|     |     |     | 420 |     |     |     |     | 425 |     |     |     |     | 430 |     |     |
| Leu | Arg | Asp | Leu | Asp | Ile | Phe | Leu | Ser | Ile | Val | Asp | Met | Asn | Glu | Gly |
|     |     | 435 |     |     |     |     | 440 |     |     |     |     | 445 |     |     |     |
| Ala | Leu | Leu | Leu | Pro | His | Phe | Asn | Ser | Lys | Ala | Ile | Val | Ile | Leu | Val |
|     | 450 |     |     |     |     | 455 |     |     |     |     | 460 |     |     |     |     |
| Ile | Asn | Glu | Gly | Asp | Ala | Asn | Ile | Glu | Leu | Val | Gly | Leu | Lys | Glu | Gln |
| 465 |     |     |     |     | 470 |     |     |     |     | 475 |     |     |     |     | 480 |
| Gln | Gln | Glu | Gln | Gln | Glu | Glu | Gln | Pro | Leu | Glu | Val | Arg | Lys | Tyr |     |
|     |     |     |     | 485 |     |     |     |     | 490 |     |     |     |     | 495 |     |
| Arg | Ala | Glu | Leu | Ser | Glu | Gln | Asp | Ile | Phe | Val | Ile | Pro | Ala | Gly | Tyr |
|     |     |     |     | 500 |     |     |     |     | 505 |     |     |     |     | 510 |     |
| Pro | Val | Val | Val | Asn | Ala | Thr | Ser | Asn | Leu | Asn | Phe | Phe | Ala | Ile | Gly |
|     |     | 515 |     |     |     |     | 520 |     |     |     |     | 525 |     |     |     |
| Ile | Asn | Ala | Glu | Asn | Asn | Gln | Arg | Asn | Phe | Leu | Ala | Gly | Ser | Gln | Asp |
|     | 530 |     |     |     |     | 535 |     |     |     |     | 540 |     |     |     |     |
| Asn | Val | Ile | Ser | Gln | Ile | Pro | Ser | Gln | Val | Gln | Glu | Leu | Ala | Phe | Pro |
| 545 |     |     |     |     | 550 |     |     |     |     | 555 |     |     |     |     | 560 |
| Gly | Ser | Ala | Gln | Ala | Val | Glu | Lys | Leu | Leu | Lys | Asn | Gln | Arg | Glu | Ser |
|     |     |     |     | 565 |     |     |     |     | 570 |     |     |     |     | 575 |     |
| Tyr | Phe | Val | Asp | Ala | Gln | Pro | Lys | Lys | Lys | Glu | Glu | Gly | Asn | Lys | Gly |
|     |     |     | 580 |     |     |     |     | 585 |     |     |     |     | 590 |     |     |
| Arg | Lys | Gly | Pro | Leu | Ser | Ser | Ile | Leu | Arg | Ala | Phe | Tyr |     |     |     |
|     |     | 595 |     |     |     |     | 600 |     |     |     |     | 605 |     |     |     |

( 2 ) INFORMATION FOR SEQ ID NO: 25:

( i ) SEQUENCE CHARACTERISTICS:
        ( A ) LENGTH: 571 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Pisum sativum ( i x ) FEATURE:
        ( A ) NAME/KEY: Protein
        ( B ) LOCATION: 1..571
        ( D ) OTHER INFORMATION: /note= "Convicilin from P. sativum"

( x i ) SEQUENCE DESCRIPTION: SEQ ID NO: 25:

| Met | Ala | Thr | Thr | Val | Lys | Ser | Arg | Phe | Pro | Leu | Leu | Leu | Phe | Leu | Gly |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Ile | Ile | Phe | Leu | Ala | Ser | Val | Cys | Val | Thr | Tyr | Ala | Asn | Tyr | Asp | Glu |

```
                        20                          25                          30
    Gly  Ser  Glu  Thr  Arg  Val  Pro  Gln  Arg  Glu  Arg  Gly  Arg  Gln  Glu
              35                      40                      45
    Gly  Glu  Lys  Glu  Glu  Lys  Arg  His  Gly  Glu  Trp  Arg  Pro  Ser  Tyr  Glu
    50                      55                      60
    Lys  Glu  Glu  His  Glu  Glu  Glu  Lys  Gln  Lys  Tyr  Arg  Tyr  Gln  Arg  Glu
    65                      70                      75                          80
    Lys  Lys  Glu  Gln  Lys  Glu  Val  Gln  Pro  Gly  Arg  Glu  Arg  Trp  Glu  Arg
                        85                      90                      95
    Glu  Glu  Asp  Glu  Glu  Gln  Val  Glu  Glu  Trp  Arg  Gly  Ser  Gln  Arg
                   100                     105                     110
    Arg  Glu  Asp  Pro  Glu  Glu  Arg  Ala  Arg  Leu  Arg  His  Arg  Glu  Glu  Arg
                   115                     120                     125
    Thr  Lys  Arg  Asp  Arg  Arg  His  Gln  Arg  Glu  Gly  Glu  Glu  Glu  Arg
         130                     135                     140
    Ser  Ser  Glu  Ser  Gln  Glu  His  Arg  Asn  Pro  Phe  Leu  Phe  Lys  Ser  Asn
    145                     150                     155                     160
    Lys  Phe  Leu  Thr  Leu  Phe  Glu  Asn  Glu  Asn  Gly  His  Ile  Arg  Arg  Leu
                        165                     170                     175
    Gln  Arg  Phe  Asp  Lys  Arg  Ser  Asp  Leu  Phe  Glu  Asn  Leu  Gln  Asn  Tyr
                   180                     185                     190
    Arg  Leu  Val  Glu  Tyr  Arg  Ala  Lys  Pro  His  Thr  Ile  Phe  Leu  Pro  Gln
              195                     200                     205
    His  Ile  Asp  Ala  Asp  Leu  Ile  Leu  Val  Val  Leu  Asn  Gly  Lys  Ala  Ile
         210                     215                     220
    Leu  Thr  Val  Leu  Ser  Pro  Asn  Asp  Arg  Asn  Ser  Tyr  Asn  Leu  Glu  Arg
    225                     230                     235                     240
    Gly  Asp  Thr  Ile  Lys  Ile  Pro  Ala  Gly  Thr  Thr  Ser  Tyr  Leu  Val  Asn
                        245                     250                     255
    Gln  Asp  Asp  Glu  Glu  Asp  Leu  Arg  Val  Val  Asp  Phe  Val  Ile  Pro  Val
                   260                     265                     270
    Asn  Arg  Pro  Gly  Lys  Phe  Glu  Ala  Phe  Gly  Leu  Ser  Glu  Asn  Lys  Asn
              275                     280                     285
    Gln  Tyr  Leu  Arg  Gly  Phe  Ser  Lys  Asn  Ile  Leu  Glu  Ala  Ser  Leu  Asn
         290                     295                     300
    Thr  Lys  Tyr  Glu  Thr  Ile  Glu  Lys  Val  Leu  Leu  Glu  Glu  Gln  Glu  Lys
    305                     310                     315                     320
    Lys  Pro  Gln  Gln  Leu  Arg  Asp  Arg  Lys  Arg  Thr  Gln  Gln  Gly  Glu  Glu
                        325                     330                     335
    Arg  Asp  Ala  Ile  Ile  Lys  Val  Ser  Arg  Glu  Gln  Ile  Glu  Glu  Leu  Arg
                   340                     345                     350
    Lys  Leu  Ala  Lys  Ser  Ser  Ser  Lys  Lys  Ser  Leu  Pro  Ser  Glu  Phe  Glu
              355                     360                     365
    Pro  Phe  Asn  Leu  Arg  Ser  His  Lys  Pro  Glu  Tyr  Ser  Asn  Lys  Phe  Gly
         370                     375                     380
    Lys  Leu  Phe  Glu  Ile  Thr  Pro  Glu  Lys  Lys  Tyr  Pro  Gln  Leu  Gln  Asp
    385                     390                     395                     400
    Leu  Asp  Ile  Leu  Val  Ser  Cys  Val  Glu  Ile  Asn  Lys  Gly  Ala  Leu  Met
                        405                     410                     415
    Leu  Pro  His  Tyr  Asn  Ser  Arg  Ala  Ile  Val  Val  Leu  Leu  Val  Asn  Glu
                   420                     425                     430
    Gly  Lys  Gly  Asn  Leu  Glu  Leu  Leu  Gly  Leu  Lys  Asn  Glu  Gln  Gln  Glu
              435                     440                     445
```

```
Arg  Glu  Asp  Arg  Lys  Glu  Arg  Asn  Asn  Glu  Val  Gln  Arg  Tyr  Glu  Ala
     450                 455                      460

Arg  Leu  Ser  Pro  Gly  Asp  Val  Val  Ile  Ile  Pro  Ala  Gly  His  Pro  Val
465                      470                      475                      480

Ala  Ile  Ser  Ala  Ser  Ser  Asn  Leu  Asn  Leu  Leu  Gly  Phe  Gly  Ile  Asn
               485                      490                           495

Ala  Lys  Asn  Asn  Gln  Arg  Asn  Phe  Leu  Ser  Gly  Ser  Asp  Asp  Asn  Val
          500                      505                     510

Ile  Ser  Gln  Ile  Glu  Asn  Pro  Val  Lys  Glu  Leu  Thr  Phe  Pro  Gly  Ser
          515                 520                      525

Ser  Gln  Glu  Val  Asn  Arg  Leu  Ile  Lys  Asn  Gln  Lys  Gln  Ser  His  Phe
     530                      535                      540

Ala  Ser  Ala  Glu  Pro  Glu  Gln  Lys  Glu  Glu  Glu  Ser  Gln  Arg  Lys  Arg
545                      550                      555                           560

Ser  Pro  Leu  Ser  Ser  Val  Leu  Asp  Ser  Phe  Tyr
               565                      570
```

( 2 ) INFORMATION FOR SEQ ID NO: 26:

( i ) SEQUENCE CHARACTERISTICS:
        ( A ) LENGTH: 410 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Pisum sativum ( i x ) FEATURE:
        ( A ) NAME/KEY: Protein
        ( B ) LOCATION: 1..410
        ( D ) OTHER INFORMATION: /note= "Vicilin from P. sativum"

( x i ) SEQUENCE DESCRIPTION: SEQ ID NO: 26:

```
Met  Leu  Leu  Ala  Ile  Ala  Phe  Leu  Ala  Ser  Val  Cys  Val  Ser  Ser  Arg
1                   5                        10                      15

Ser  Asp  Gln  Glu  Asn  Pro  Phe  Ile  Phe  Lys  Ser  Asn  Arg  Phe  Gln  Thr
               20                      25                      30

Leu  Tyr  Glu  Asn  Glu  Asn  Gly  His  Ile  Arg  Leu  Leu  Gln  Lys  Phe  Asp
          35                      40                           45

Lys  Arg  Ser  Lys  Ile  Phe  Glu  Asn  Leu  Gln  Asn  Tyr  Arg  Leu  Leu  Glu
     50                      55                      60

Tyr  Lys  Ser  Lys  Pro  His  Thr  Leu  Phe  Leu  Pro  Gln  Tyr  Thr  Asp  Ala
65                       70                      75                           80

Asp  Phe  Ile  Leu  Val  Val  Leu  Ser  Gly  Lys  Ala  Thr  Leu  Thr  Val  Leu
               85                      90                           95

Lys  Ser  Asn  Asp  Arg  Asn  Ser  Phe  Asn  Leu  Glu  Arg  Gly  Asp  Ala  Ile
               100                     105                     110

Lys  Leu  Pro  Ala  Gly  Ser  Ile  Ala  Tyr  Phe  Ala  Asn  Arg  Asp  Asp  Asn
          115                     120                     125

Glu  Glu  Pro  Arg  Val  Leu  Asp  Leu  Ala  Ile  Pro  Val  Asn  Lys  Pro  Gly
     130                     135                     140

Gln  Leu  Gln  Ser  Phe  Leu  Leu  Ser  Gly  Thr  Gln  Asn  Gln  Lys  Ser  Ser
145                     150                     155                          160

Leu  Ser  Gly  Phe  Ser  Lys  Asn  Ile  Leu  Glu  Ala  Ala  Phe  Asn  Thr  Asn
               165                     170                     175

Tyr  Glu  Glu  Ile  Glu  Lys  Val  Leu  Leu  Glu  Gln  Gln  Glu  Gln  Glu  Pro
               180                     185                     190
```

```
Gln His Arg Arg Ser Leu Lys Asp Arg Arg Gln Glu Ile Asn Glu Glu
        195                 200                 205

Asn Val Ile Val Lys Val Ser Arg Asp Gln Ile Glu Glu Leu Ser Lys
225     210             215                 220

Asn Ala Lys Ser Ser Lys Lys Ser Val Ser Ser Glu Ser Gly Pro
225                 230                 235                 240

Phe Asn Leu Arg Ser Arg Asn Pro Ile Tyr Ser Asn Lys Phe Gly Lys
                245                 250                 255

Phe Phe Glu Ile Thr Pro Glu Lys Asn Gln Leu Gln Asp Leu Asp
            260             265                 270

Ile Phe Val Asn Ser Val Asp Ile Lys Val Gly Ser Leu Leu Leu Pro
        275                 280                 285

Asn Tyr Asn Ser Arg Ala Ile Val Ile Val Thr Val Thr Glu Gly Lys
        290             295                 300

Gly Asp Phe Glu Leu Val Gly Gln Arg Asn Glu Asn Gln Gly Lys Glu
305                 310                 315                 320

Asn Asp Lys Glu Glu Gln Glu Glu Glu Thr Ser Lys Gln Val Gln
                325                 330                 335

Leu Tyr Arg Ala Lys Leu Ser Pro Gly Asp Val Phe Val Ile Pro Ala
            340                 345                 350

Gly His Pro Val Ala Ile Asn Ala Ser Ser Asp Leu Asn Leu Ile Gly
        355                 360                 365

Leu Gly Ile Asn Ala Glu Asn Asn Glu Arg Asn Phe Leu Ala Gly Glu
        370                 375                 380

Glu Asp Asn Val Ile Ser Gln Val Glu Arg Pro Val Lys Glu Leu Ala
385                 390                 395                 400

Phe Pro Gly Ser Ser His Glu Val Asp Arg
                405                 410
```

(2) INFORMATION FOR SEQ ID NO: 27:

(i) SEQUENCE CHARACTERISTICS:
  (A) LENGTH: 421 amino acids
  (B) TYPE: amino acid
  (D) TOPOLOGY: linear (ii) MOLECULE TYPE: protein (vi) ORIGINAL SOURCE:
  (A) ORGANISM: Phaseolus vulgaris (ix) FEATURE:
  (A) NAME/KEY: Protein
  (B) LOCATION: 1..421
  (D) OTHER INFORMATION: /note= "Vicilin from P. vulgaris"

(xi) SEQUENCE DESCRIPTION: SEQ ID NO: 27:

```
Met Met Arg Ala Arg Val Pro Leu Leu Leu Leu Gly Ile Leu Phe Leu
1               5                   10                  15

Ala Ser Leu Ser Ala Ser Phe Ala Thr Ser Leu Arg Glu Glu Glu Glu
                20                  25                  30

Ser Gln Asp Asn Pro Phe Tyr Phe Asn Ser Asp Asn Ser Trp Asn Thr
            35                  40                  45

Leu Phe Lys Asn Gln Tyr Gly His Ile Arg Val Leu Gln Arg Phe Asp
        50                  55                  60

Gln Gln Ser Lys Arg Leu Gln Asn Leu Glu Asp Tyr Arg Leu Val Glu
65                  70                  75                  80

Phe Arg Ser Lys Pro Glu Thr Leu Leu Leu Pro Gln Gln Ala Asp Ala
                85                  90                  95
```

|     |     |     |     |     |     |     |     |     |     |     |     |     |     |     |
|-----|-----|-----|-----|-----|-----|-----|-----|-----|-----|-----|-----|-----|-----|-----|
| Glu | Leu | Leu | Leu<br>100 | Val | Val | Arg | Ser | Gly<br>105 | Ser | Ala | Ile | Leu | Val<br>110 | Leu | Val |
| Lys | Pro | Asp<br>115 | Asp | Arg | Arg | Glu | Tyr<br>120 | Phe | Phe | Leu | Thr | Ser<br>125 | Asp | Asn | Pro |
| Ile | Phe | Ser | Asp<br>130 | His | Gln | Lys<br>135 | Ile | Pro | Ala | Gly | Thr<br>140 | Ile | Phe | Tyr | Leu |
| Val<br>145 | Asn | Pro | Asp | Pro | Lys<br>150 | Glu | Asp | Leu | Arg | Ile<br>155 | Ile | Gln | Leu | Ala | Met<br>160 |
| Pro | Val | Asn | Asn | Pro<br>165 | Gln | Ile | His | Glu | Phe<br>170 | Phe | Leu | Ser | Ser | Thr<br>175 | Glu |
| Ala | Gln | Gln | Ser<br>180 | Tyr | Leu | Gln | Glu | Phe<br>185 | Ser | Lys | His | Ile | Leu<br>190 | Glu | Ala |
| Ser | Phe | Asn<br>195 | Ser | Lys | Phe | Glu | Glu<br>200 | Ile | Asn | Arg | Val | Leu<br>205 | Phe | Glu | Glu |
| Glu | Gly<br>210 | Gln | Gln | Glu | Gly | Val<br>215 | Ile | Val | Asn | Ile | Asp<br>220 | Ser | Glu | Gln | Ile |
| Lys<br>225 | Glu | Leu | Ser | Lys | His<br>230 | Ala | Lys | Ser | Ser | Ser<br>235 | Arg | Lys | Ser | Leu | Ser<br>240 |
| Lys | Gln | Asp | Asn | Thr<br>245 | Ile | Gly | Asn | Glu | Phe<br>250 | Gly | Asn | Leu | Thr | Glu<br>255 | Arg |
| Thr | Asp | Asn | Ser<br>260 | Leu | Asn | Val | Leu | Ile<br>265 | Ser | Ser | Ile | Glu | Met<br>270 | Glu | Glu |
| Gly | Ala | Leu<br>275 | Phe | Val | Pro | His | Tyr<br>280 | Tyr | Ser | Lys | Ala | Ile<br>285 | Val | Ile | Leu |
| Val | Val<br>290 | Asn | Glu | Gly | Glu | Ala<br>295 | His | Val | Glu | Leu | Val<br>300 | Gly | Pro | Lys | Gly |
| Asn<br>305 | Lys | Glu | Thr | Leu | Glu<br>310 | Tyr | Glu | Ser | Tyr | Arg<br>315 | Ala | Glu | Leu | Ser | Lys<br>320 |
| Asp | Asp | Val | Phe | Val<br>325 | Ile | Pro | Ala | Ala | Tyr<br>330 | Pro | Val | Ala | Ile | Lys<br>335 | Ala |
| Thr | Ser | Asn | Val<br>340 | Asn | Phe | Thr | Gly | Phe<br>345 | Gly | Ile | Asn | Ala | Asn<br>350 | Asn | Asn |
| Asn | Arg | Asn<br>355 | Leu | Leu | Ala | Gly | Lys<br>360 | Thr | Asp | Asn | Val | Ile<br>365 | Ser | Ser | Ile |
| Gly | Arg<br>370 | Ala | Leu | Asp | Gly | Lys<br>375 | Asp | Val | Leu | Gly | Leu<br>380 | Thr | Phe | Ser | Gly |
| Ser<br>385 | Gly | Asp | Glu | Val | Met<br>390 | Lys | Leu | Ile | Asn | Lys<br>395 | Gln | Ser | Gly | Ser | Tyr<br>400 |
| Phe | Val | Asp | Ala | His<br>405 | His | His | Gln | Gln | Glu<br>410 | Gln | Gln | Lys | Gly | Arg<br>415 | Lys |
| Gly | Ala | Phe | Val<br>420 | Tyr | | | | | | | | | | | |

( 2 ) INFORMATION FOR SEQ ID NO: 28:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO: 28:

GGAGACTGCC ATGG                                          14

RECOMBINANT 47 AND 31KD COCOA PROTEINS AND PRECURSOR

This application is filed under 35 USC §371 as the national stage of PCT/G891/00914 filed Jun. 7, 1991.

This invention relates to proteins and nucleic acids derived from or otherwise related to cocoa.

The beans of the cocoa plant (*Theobroma cacao*) are the raw material for cocoa, chocolate and natural cocoa and chocolate flavouring. As described by Rohan ("Processing of Raw Cocoa for the Market", FAO/UN (1963)), raw cocoa beans are extracted from the harvested cocoa pod, from which the placenta is normally removed, the beans are then "fermented" for a period of days, during which the beans are killed and a purple pigment is released from the cotyledons. During fermentation "unknown" compounds are formed which on roasting give rise to characteristic cocoa flavour. Rohan suggests that polyphenols and theobromine are implicated in the flavour precursor formation. After fermentation, the beans are dried, during which time the characteristic brown pigment forms, and they are then stored and shipped.

Biehl et al. 1982 investigated proteolysis during anaerobic cocoa seed incubation and identified 26 kD and 44 kD proteins which accumulated during seed ripening and degraded during Germination. Biehl asserted that there were storage proteins and suggested that they may give rise to flavour-specific peptides.

Fritz et al, 1985 identified polypeptides of 20 kD and 28 kD appearing in the cytoplasmic fraction of cocoa seed extracts at about 100 days after pollination. It appears that the 20 kD protein is thought to have glyceryl acyltransferase activity.

In spite of the uncertainties in the art, as summarised above, proteins apparently responsible for flavour production in cocoa beans have now been identified. Further, it has been discovered that, in spite of Fritz's caution that "cocoa seed mRNA levels are notably low compared to other plants" (loc. cit.), it is possible to apply the techniques of recombinant DNA techniques to the production of such proteins.

According to a first aspect of the invention, there is provided a 67 kD protein of *Theobroma cacao*, or a fragment thereof.

The 67 kD protein appears to be a primary translation product of interest in proteins involved in flavour production in cocoa. The 67 kD protein may be processed in vivo to form 47 kD and 31 kD polypeptides.

According to a second aspect of the invention, there is provided a 47 kD protein of *Th. cacao*, or a fragment thereof.

According to a third aspect of the invention, there is provided a 31 kD protein of *Th. cacao* or a fragment thereof.

The term "fragment" as used herein and as applied to proteins or peptides indicates a sufficient number of amino acid residues are present for the fragment to be useful. Typically, at least four, five, six or even at least 10 or 20 amino acids may be present in a fragment. Useful fragments include those which are the same as or similar or equivalent to those naturally produced during the fermentation phase of cocoa bean processing. It is believed that such fragments take part in Maillard reactions during roasting, to form at least some of the essential flavour components of cocoa.

Proteins in accordance with the invention may be synthetic; they may be chemically synthesised or, preferably, produced by recombinant DNA techniques. Proteins produced by such techniques can therefore be termed "recombinant proteins". Recombinant proteins may be glycosylated or non-glycosylated: non-glycosylated proteins will result from prokaryotic expression systems. *Theobroma cacao* has two primary subspecies, *Th. cacao cacao* and *Th. cacao sphaerocarpum*. While proteins in accordance with the invention may be derived from these subspecies, the invention is not limited solely to these subspecies. For example, many cocoa varieties are hybrids between different species; an example of such a hybrid is the trinitario variety.

The invention also relates to nucleic acid, particularly DNA, coding for the proteins referred to above (whether the primary translation products, the processed proteins or fragments). The invention therefore also provides, in further aspects:

nucleic acid coding for a 67 kD protein of *Th. cacao*, or for a fragment thereof:

nucleic acid coding for a 47 kD protein of *Th. cacao*, or for a fragment thereof;

nucleic acid coding for a 31 kD protein of *Th. cacao*, or for a fragment thereof:

Included in the invention is nucleic acid which is degenerate for the wild type protein and which codes for conservative or other non-deleterious mutants. Nucleic acid which hybridises to the wild type material is also included.

Nucleic acid within the scope of the invention will generally be recombinant nucleic acid and may be in isolated form. Frequently, nucleic acid in accordance with the invention will be incorporated into a vector (whether an expression vector or otherwise) such as a plasmid. Suitable expression vectors will contain an appropriate promoter, depending on the intended expression host. For yeast, an appropriate promoter is the yeast pyruvate kinase (PK) promoter; for bacteria an appropriate promoter is a strong lambda promoter.

Expression may be secreted or non-secreted. Secreted expression is preferred, particularly in eukaryotic expression systems; an appropriate signal sequence may be present for this purpose. Signal sequences derived from the expression host (such as that from the yeast alpha-factor in the case of yeast) may be more appropriate than native cocoa signal sequences.

The invention further relates to host cells comprising nucleic acid as described above. Genetic manipulation may for preference take place in prokaryotes. Expression will for preference take place in a food-approved host. The yeast *Saccharomyces cerevisiae* is particularly preferred.

The invention also relates to processes for preparing nucleic acid and protein as described above by nucleic acid replication and expression, respectively.

cDNA in accordance with the invention may be useful not only for obtaining protein expression but also for Restriction Fragment Length Polymorphism (RFLP) studies. In such studies, detectably labelled cDNA (eg radiolabelled) is prepared. DNA of a cultivar under analysis is then prepared and digested with restriction enzymes. Southern blotting with the labelled cDNA may then enable genetic correlations to be made between cultivars. Phenotypic correlations may then be deduced.

The invention will now be illustrated by the following non-limiting examples. The examples refer to the accompanying drawings, in which: FIG. 1 shows a map of the coding region of the 67 kD protein, together with the inter-relationship of plasmids pMS600, pMS700 and pMS800, from which sequence data were obtained;

FIGS. 2A–2D (SEQ ID NOS: 1 and 2) shows the complete nucleotide sequence of cDNA coding for the 67 kD protein and the deduced amino acid sequence;

FIG. 3 (SEQ ID NO:22) shows the amino acid sequence referred to in FIG. 2;

Figure 4A:
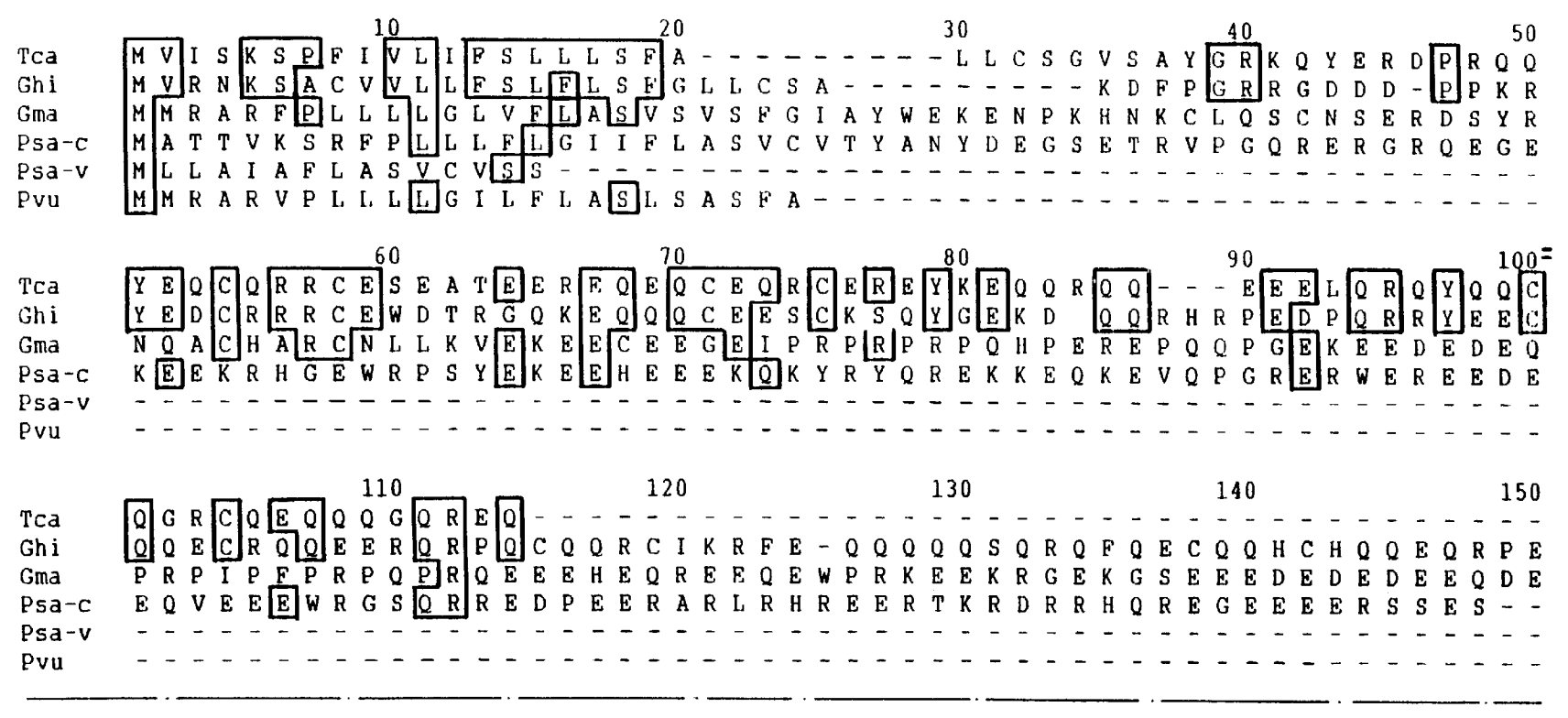
Figure 4B:
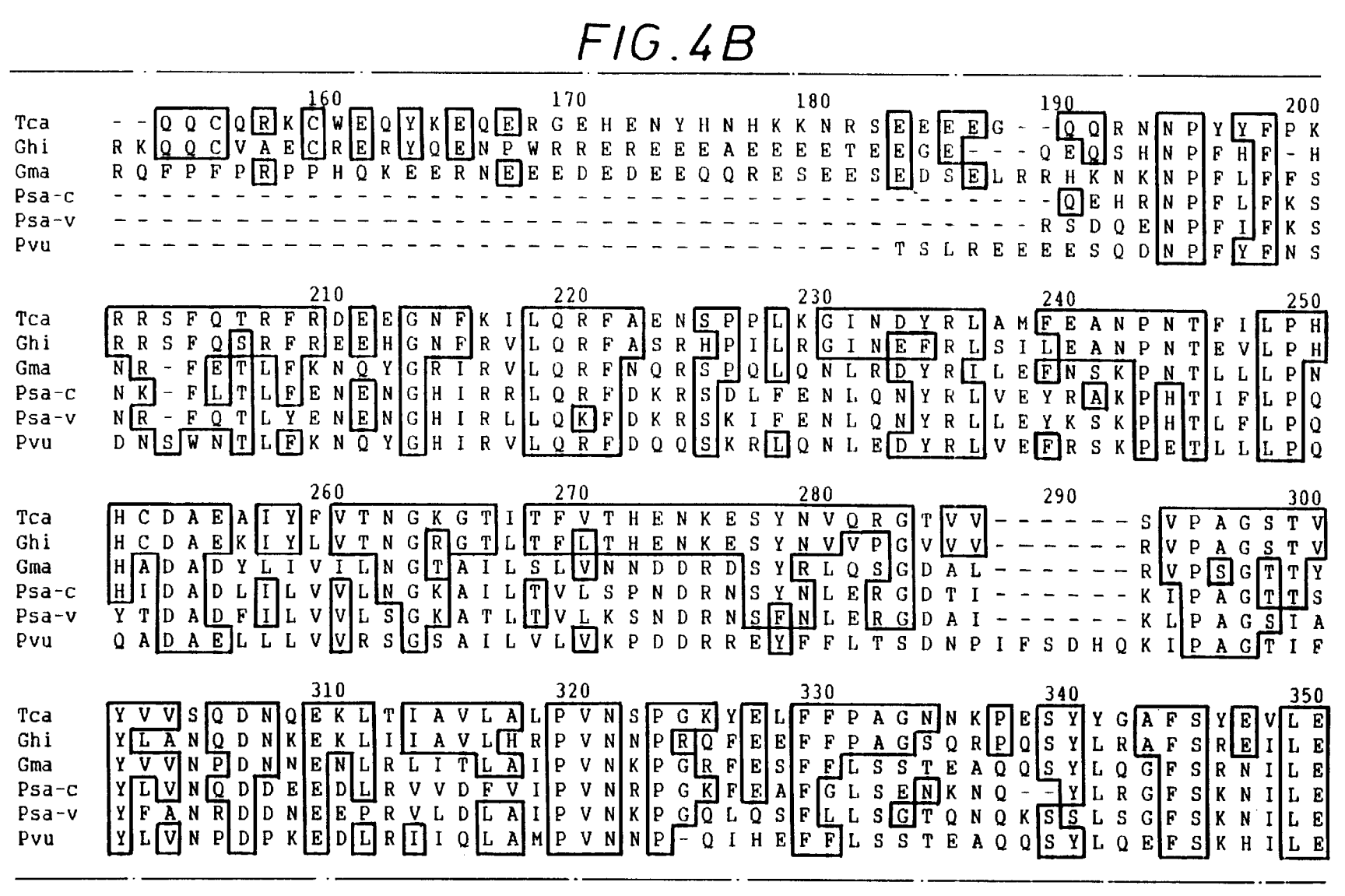
Figure 4C:
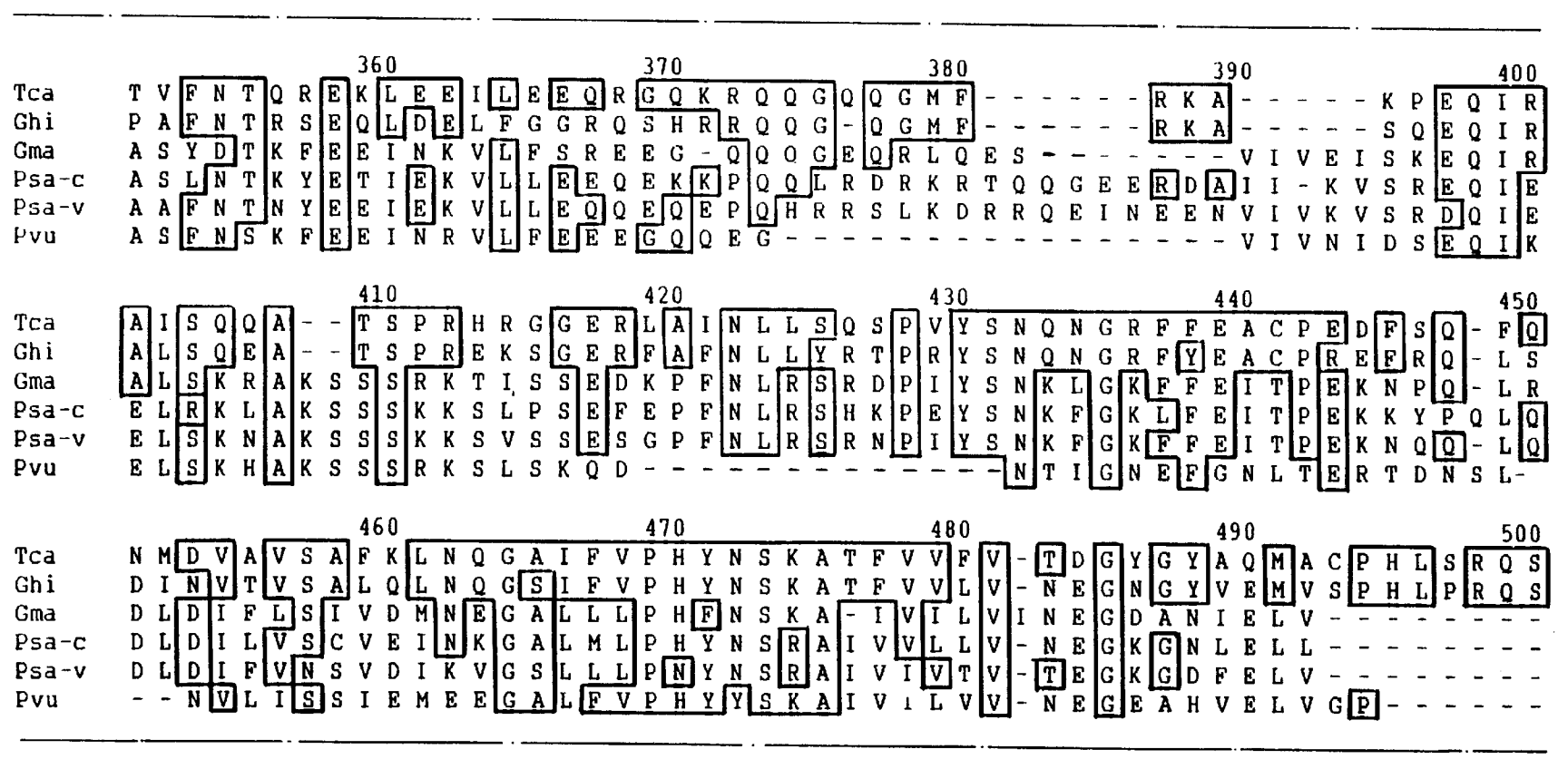
Figure 4D:
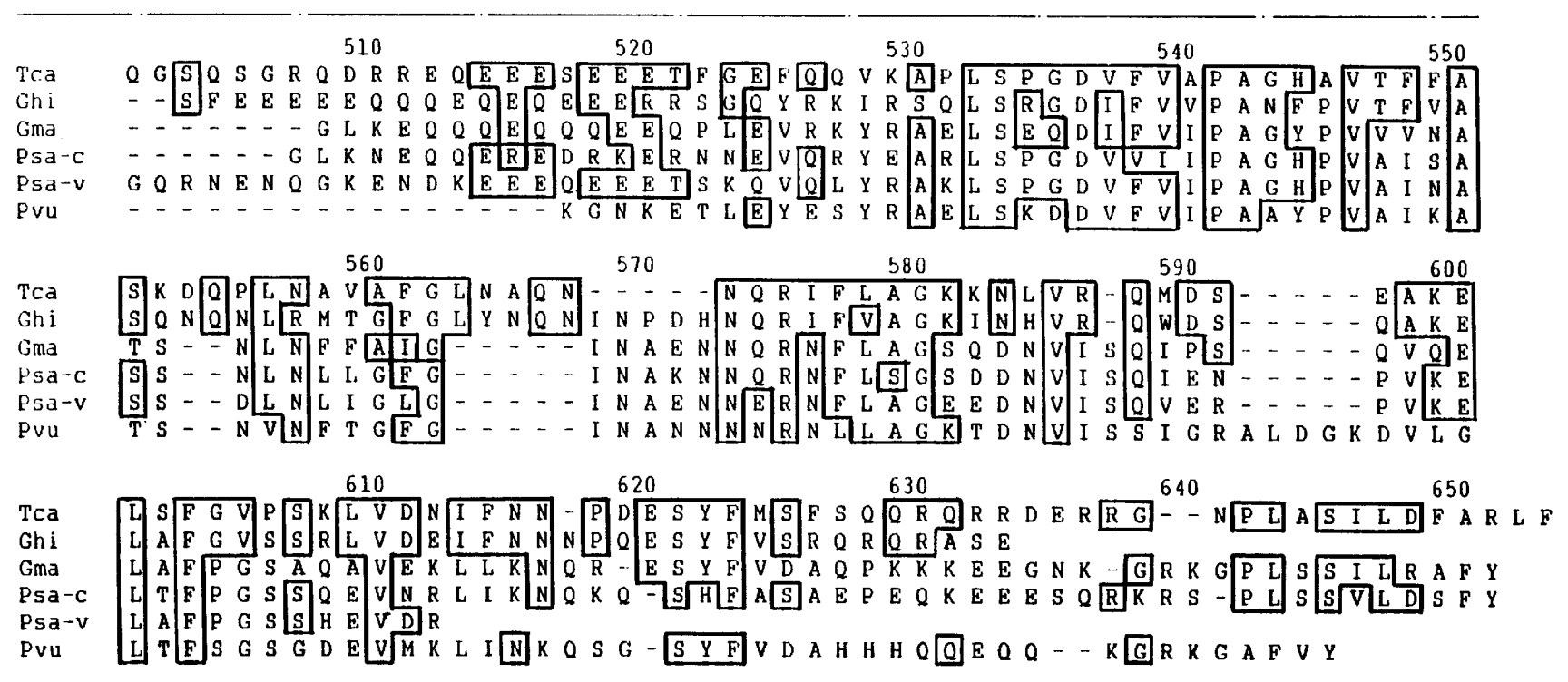

FIGS. 4A–4D (SEQ ID NOS: 22–27) shows the relationship between the 67 kD protein and seed storage proteins from other plants;

FIG. 7 shows two yeast expression vectors useful in the present invention; vector A is designed for internal expression and vector B is designed for secreted expression;

FIG. 8a (SEQ ID NOS:4–11) shows, in relation to vector A, part of the yeast pyruvate kinase gene showing the vector A cloning site, and the use of Hin-Nco linkers to splice in the heterologous gene;

FIG. 8b (SEQ ID NOS:12–17) shows, in relation to vector B, part of the yeast alpha-factor signal sequence showing the vector B cloning site, and the use of Hin-Nco linkers to create an in-phase fusion;

FIG. 9b shows how plasmid pMS903 can be manipulated to produce plasmids pMS904, pMS905, pMS906, pMS909 and pMS916;

FIG. 10 shows maps of plasmids pMS908, pMS914, pMS912, pMS906, pMS916 and pMS910;

EXAMPLES

Figure 1:
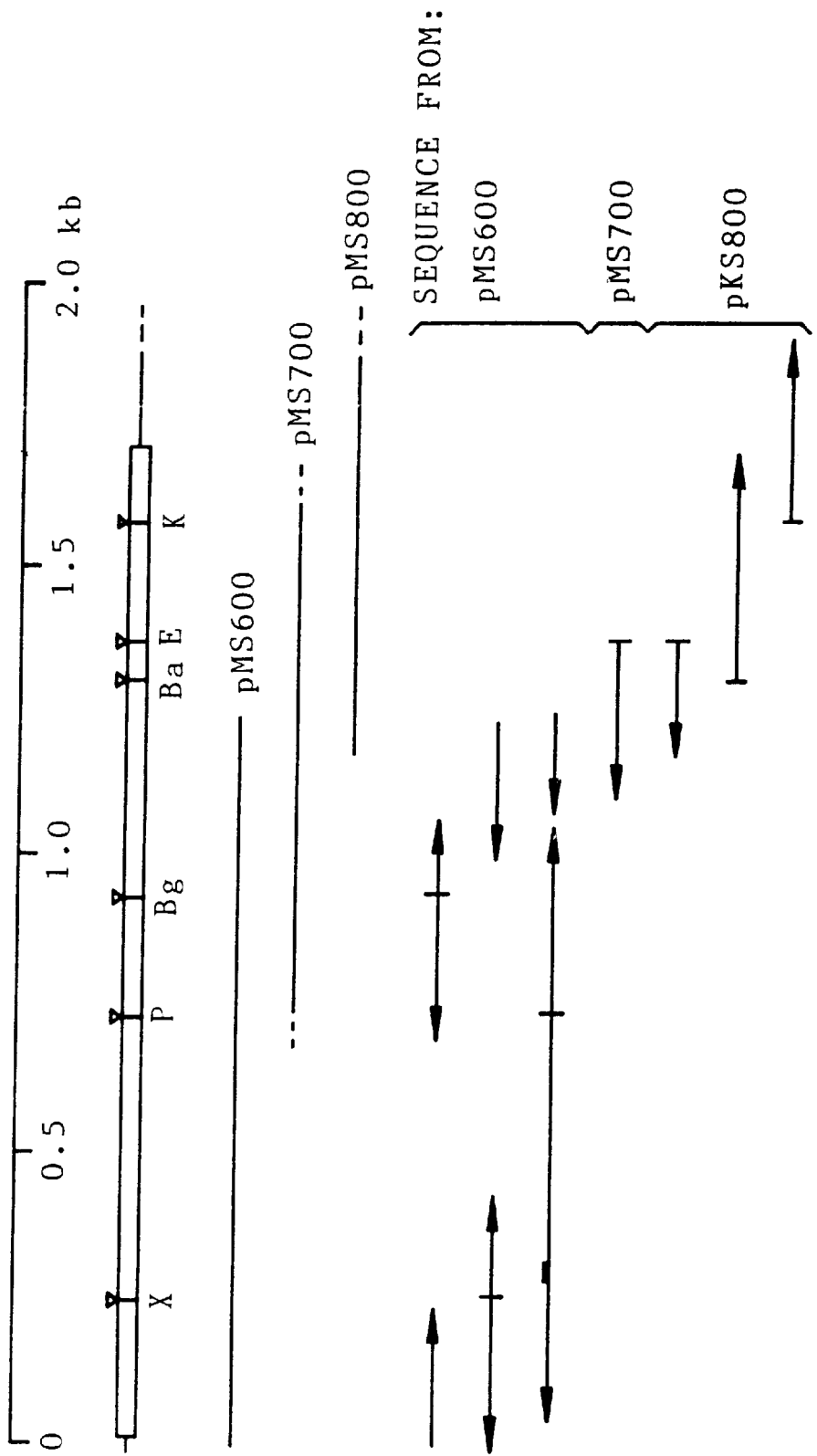

Example 1
Identification of the Major Seed Proteins

It is not practicable to extract proteins directly from cocoa beans due to the high fat and polyphenol contents, and proteins were, therefore, extracted from acetone powders made as follows. Mature beans from cocoa of West African origin (*Theobroma cacao amelonada*) were lyophilised and ground roughly in a pestle and mortar. Lipids were extracted by Soxhlet extraction with diethyl ether for two periods of four hours, the beans being dried and further ground between extractions. Polyphenols and pigments were then removed by several extractions with 80% acetone. 0.1% thioglycollic acid. After extraction the resulting paste was dried under vacuum and ground to a fine powder.

Total proteins were solubilised by grinding the powder with extraction buffer (0.05M sodium phosphate. pH 7.2; 0.01M 2-mercaptoethanol; 1% SDS) in a hand-held homogeniser, at 5 mg/ml The suspension was heated at 95° C. for 5 minutes, and centrifuged at 18K for 20 minutes to remove insoluble material. The resulting clear supernatant contained about 1 mg/ml total protein. Electrophoresis of 25 μl on an SDS-PAGE gel (Laemmli, 1970) gave three major bands, two of which were at 47 kD and 31 kD, comprising over 60% of the total proteins. The 47 kD and 31 kD proteins are presumed to be the polypeptide subunits of major storage proteins.

Characteristics of the Storage Polypeptides

The solubility characteristics of the 47 kD and 31 kD polypeptides were roughly defined by one or two quick experiments. Dialysis of the polypeptide solution against SDS-free extraction buffer rendered the 47 kD and 31 kD polypeptides insoluble, as judged by their ability to pass through a 0.22 micron membrane. Fast Protein Liquid Chromatography (FPLC) analysis also showed that the 47 kD and 31 kD polypeptides were highly associated after extraction with McIlvaines buffer pH 6.8 (0.2M disodium hydrogen phosphate titrated with 0.1M citric acid). The 47 kD and 31 kD polypeptides are globulins on the basis on their solubility.

Purification of the 47 kD and 31 kD polypeptides

The 47 kD and 31 kD polypeptides were purified by two rounds of gel filtration on a SUPEROSE-12 column of the PHARMACIA Fast Protein Liquid Chromatography system (FPLC), or by electroelution of bands after preparative electrophoresis. (The words SUPEROSE and PHARMACIA are trade marks.) Concentrated protein extracts were made from 50 mg acetone powder per ml of extraction buffer, and 1–2 ml loaded onto 2 mm thick SDS-PAGE gels poured without a comb. After electrophoresis the gel was surface stained in aqueous Coomassie Blue, and the 47 kD and 31 kD bands cut out with a scalpel. Gel slices were electroeluted into dialysis bags in electrophoresis running buffer at 15 V for 24 hours, and the dialysate dialysed further against 0.1 % SDS. Samples could be concentrated by lyophilisation.

Example 2
Amino-acid Sequence Data from Proteins

Protein samples (about 10 μg) were subjected to conventional N-terminal amino-acid sequencing. The 47 kD and 31 kD polypeptides were N-terminally blocked, so cyanogen bromide peptides of the 47 kD and 31 kD peptides were prepared, and some amino-acid sequence was derived from these. Cyanogen bromide cleaves polypeptide chains at methionine residues, and thus cleaved the 47 kD and 31 kD polypeptides gave rise to 24 kD and 17 kD peptides. In addition the 47 kD polypeptide gave a 20 kD peptide. The 24 kD and 17 kD peptides had the same 9 N-terminal amino-acid residues. This fact, combined with the obvious one that the 31 kD could not contain both peptides consecutively, suggested that the 24 kD peptide arose for a partial digest, where full digestion would yield the 17 kD peptide. The other striking conclusion is that the 47 kD and 31 kD proteins are related, and the 31 kD could be a further processed form of the 47 kD. The 9 amino-acid sequence was used to construct an oligonucleotide probe for the 47 kD/3 1 kD gene(s).

Example 3
Raising Antibodies to the 47 kD and 31 kD Polypeptides

Polyclonal antibodies were prepared using the methodology of Catty and Raykundalia (1988). The serum was aliquoted into 1 ml fractions and stored at −20° C.

Characterising Antibodies to the 47 kD and 31 kD Polypeptides

Serum was immediately characterised using the Ochterloney double-diffusion technique, whereby antigen and antibody are allowed to diffuse towards one another from wells cut in agarose in borate-saline buffer. Precipitin lines are formed where the two interact if the antibody 'recognises' the antigen. This test showed that antibodies to both antigens had been formed, and furthermore that extensive cross-reaction took place between the 47 kD and 31 kD polypeptides and their respective antibodies. This is further indication that the 47 kD and 31 kD polypeptides are closely related, as suggested by their cyanogen bromide cleavage patterns.

The gamma-globulin fraction of the serum was partially purified by precipitation with 50% ammonium sulphate, solubilisation in phosphate-buffered saline (PBS) and chromatography on a DE 52 cellulose ion-exchange column as described by Hill, 1984. Fractions containing gamma-globulin were monitored at 280 nm ($OD_{280}$ of 1.4 is equivalent to 1 mg/ml gamma-globulin) and stored at −20° C. The effective titre of the antibodies was measured using an enzyme-linked immunosorbant assay (ELISA). The wells of a polystyrene microtitre plate were coated with antigen (10–1000 ng) overnight at 4° C. in carbonate coating buffer. Wells were washed in PBS-Tween and the test gamma globulin added at concentrations of 10, 1 and 0.1 µg/ml (approximately 1:100, 1:1000 and 1:10,000 dilutions). The diluent was PBS-Tween containing 2% polyvinyl pyrrolidone (PVP) and 0.2% BSA. Controls were preimmune serum from the same animal. Binding took place at 37° C. for 3–4 hours. The wells were washed as above and secondary antibody (goat anti-rabbit IgG conjugated to alkaline phosphatase) added at a concentration of 1 µg/ml, using the same conditions as the primary antibody. The wells are again washed, and alkaline phosphatase substrate (p-nitrophenyl phosphate pH 0.6 mg/ml in diethanol-amine buffer pH 9.8) added. The yellow colour, indicating a positive reaction, was allowed to develop for 30 minutes and the reaction stopped with 3M NaOH. The colour is quantified at 405 nm. More detail of this method is given in Hill, 1984. The method confirmed that the antibodies all had a high titre and could be used at 1 µg/ml concentration.

Example 4
Isolation of Total RNA from Immature Cocoa Beans

The starting material for RNA which should contain a high proportion of mRNA specific for the storage proteins was immature cocoa beans, at about 130 days after pollination. Previous work had suggested that synthesis of storage proteins was approaching its height by this date (Biehl et al, 1982). The beans are roughly corrugated and pale pinkish-purple at this age.

The initial requirement of the total RNA preparation from cocoa beans was that it should be free from contaminants, as judged by the UV spectrum, particularly in the far UV, where a deep trough at 230 nm (260 nm:230 nm ratio is approximately 2.0) is highly diagnostic of clean RNA, and is intact, as judged by agarose gel electrophoresis of heat-denatured samples, which should show clear rRNA bands. A prerequisite for obtaining intact RNA is scrupulous cleanliness and rigorous precautions against RNases, which are ubiquitous and extremely stable enzymes. Glassware is customarily baked at high temperatures, and solutions and apparatus treated with the RNase inhibitor diethyl pyrocarbonate (DEPC, 0.1%) before autoclaving.

The most routine method for extraction of plant (and animal) RNA is extraction of the proteins with phenol/chloroform in the presence of SDS to disrupt protein-nucleic acid complexes, and inhibit the RNases which are abundant in plant material. Following phenol extraction the RNA is pelletted on a caesium chloride gradient before or after ethanol precipitation. This method produced more or less intact RNA, but it was heavily contaminated with dark brown pigment, probably oxidised polyphenols and tannins, which always co-purified with the RNA. High levels of polyphenols are a major problem in Theobroma tissues.

A method was therefore adopted which avoided the use of phenol, and instead used the method of Hall et al. (1978) which involves breaking the tissue in hot SDS-borate buffer, digesting the proteins with proteinase K, and specifically precipitating the RNA with LiCl. This method gave high yields of reasonably clean, intact RNA. Contaminants continued to be a problem and the method was modified by introducing repeated LiCl precipitation steps, the precipitate being dissolved in water and clarified by microcentrifugation after each step. This resulted in RNA preparations with ideal spectra, which performed well in subsequent functional tests such as in vitro translation.

Preparation of mRNA From Total RNA

The mRNA fraction was separated from total RNA by affinity chromatography on a small (1 ml) oligo-dT column, the mRNA binding to the column by its poly A tail. The RNA (1–2 mg) was denatured by heating at 65° C. and applied to the column in a high salt buffer. Poly A+was eluted with low salt buffer, and collected by ethanol precipitation. The method is essentially that of Aviv and Leder (1972), modified by Maniatis et al (1982). From 1 mg of total RNA, approximately 10–20 g polyA+RNA was obtained (1–2%).

In vitro Translation of mRNA

The ability of mRNA to support in vitro translation is a good indication of its cleanliness and intactness. Only mRNAs with an intact polyA tail (3' end) will be selected by the oligo-dT column, and only mRNAs which also have an intact 5' end (translational start) will translate efficiently. In vitro translation was carried out using RNA-depleted wheatgerm lysate (Amersham International), the de novo protein synthesis being monitored by the incorporation of $[^{35}S]$-methionine (Roberts and Paterson, 1973). Initially the rate of de novo synthesis was measured by the incorporation of $[^{35}S]$-methionine into TCA-precipitable material trapped on glass fibre filters (GFC, Whatman). The actual products of translation were investigated by running on SDS-PAGE, soaking the gel in fluor, drying the gel and autoradiography. The mRNA preparations translated efficiently and the products covered a wide range of molecular weights, showing that intact mRNAs for even the largest proteins had been obtained. None of the major translation products corresponded in size to the 47 kD or 3 kD storage polypeptides identified in mature beans, and it was apparent that considerable processing of the nascent polypeptides must occur to give the mature forms.

Example 5
Identification of Precursor to the 47 kD and 31 kD Polypeptides by Immunoprecipitation Because the 47 kD and 31 kD storage polypeptides were not apparent amongst the translation products of mRNA from developing cocoa beans, the technique of immunoprecipitation, with specific antibodies raised to the storage polypeptides, was used to identify the precursors from the translation mixture. This was done for two reasons: first to confirm that the appropriate mRNA was present before cloning, and second to gain information on the expected size of the encoding genes.

Immunoprecipitation was by the method of Cuming et al, 1986. $[^{35}S]$-labelled in vitro translation products were dissociated in SDS, and allowed to bind with specific antibody in PBS plus 1% BSA. The antibody-antigen mixture was then mixed with protein A-SEPHAROSE and incubated on ice to allow the IgG to bind to protein A. The slurry was poured into a disposable 1 ml syringe, and unbound proteins removed by washing with PBS+1% NONIDET P-40. The bound antibody was eluted with 1M acetic acid and the proteins precipitated with TCA. The antibody-antigen complex was dissociated in SDS, and subject to SDS-PAGE and fluorography, which reveals which labelled antigens have bound to the specific antibodies.

The results showed that the anti-47 kD and anti-31 kD antibodies both precipitated a 67 kD precursor. The precursor size corresponded to a major band on the in vitro translation products. The results with the 47 kD and 31 kD antibodies confirmed that the polypeptides are derived from a single precursor, or at least precursors of the same size. The large size of the precursor suggested that size-selection at mRNA or cDNA level may be necessary to obtain clones.

Example 6
cDNA Synthesis From the mRNA Preparations cDNA synthesis was carried out using a kit from Amersham International. The first strand of the cDNA is synthesised by the enzyme reverse transcriptase, using the four nucleotide bases found in DNA (dATP, dTTP, dGTP, dCTP) and an oligo-dT primer. The second strand synthesis was by the method of Gubler and Hoffman (1983), whereby the RNA strand is nicked in many positions by RNase H, and the remaining fragments used to prime the replacement synthesis of a new DNA strand directed by the enzyme E. coli DNA polymerase I. Any 3' overhanging ends of DNA are filled in using the enzyme T4 polymerase. The whole process was monitored by adding a small proportion of [$^{32}$P]-dCTP into the initial nucleotide mixture, and measuring the percentage incorporation of label into DNA. Assuming that cold nucleotides are incorporated at the same rate, and that the four bases are incorporated equally, an estimate of the synthesis of cDNA can be obtained. From 1μg of mRNA approximately 140 ng of cDNA was synthesised. The products were analysed on an alkaline 1.4% agarose gel as described in the Amersham methods. Globin cDNA, synthesised as a control with the kit, was run on the same gel, which was dried down and autoradiographed. The cocoa cDNA had a range of molecular weights, with a substantial amount larger than the 600 bp of the globin cDNA.

Example 7
Cloning of cDNA into a Plasmid Vector by Homopolymer Tailing

The method of cloning cDNA into a plasmid vector was to 3' tail the cDNA with dC residues using the enzyme terminal transferase (Boehringer Corporation Ltd), and anneal into a PstI-cut and 5' tailed plasmid (Maniatis et al, 1982 Eschenfeldt et al. 1987). The optimum length for the dC tail is 12–20 residues. The tailing reaction (conditions as described by the manufacturers) was tested with a 1.5 kb blunt-ended restriction fragment, taking samples at intervals, and monitoring the incorporation of a small amount of [$^{32}$P]-dCTP. A sample of cDNA (70 ng) was then tailed using the predetermined conditions.

A dG-tailed plasmid vector (3'-oligo(dG)-tailed pUC9) was purchased from Pharmacia. 15 ng vector was annealed with 0.5–5 ng of cDNA at 58° C. for 2 hours in annealing buffer:5 mM Tris-HCl pH 7.6; 1 mM EDTA, 75 mM NaCl in a total volume of 50 μl. The annealed mixture was transformed into E. coli RRI (Bethesda Research Laboratories), transformants being selected on L-agar +100 μg/ml ampicillin. Approximately 200 transformants per ng of cDNA were obtained. Transformants were stored by growing in 100 1μl L-broth in the wells of microtitre plates, adding 100 μl 80% glycerol, and storing at −20° C.

Some of the dC tailed cDNA was size selected by electrophoresing on a 0.8% agarose gel, cutting slits in the gel at positions corresponding to 0.5, 1.0 and 1.5 kb, inserting DE81 paper and continuing electrophoresis until the cDNA had run onto the DE81 paper. The DNA was then eluted from the paper with high salt buffer, according to the method of Dretzen et al (1981).

Example 8
Construction of Oligonucleotide Probes for the 47131 kD Gene

The amino-acid sequence (SEQ ID NO:18) obtained from a cyanogen bromide peptide common to the 47 kD and 31 kD polypeptides is as follows:

Met-Phe-Glu-Ala-Asn-Pro-Asn-Thr-Phe and the least redundant probe of 17 residues (a mixture of 32) (SEQ ID NO:19) is shown below:

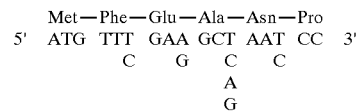

The actual probe was made anti-sense so that it could also be used to probe mRNA. Probe synthesis was carried out using an Applied Biosystems apparatus.

Example 9
Use of Oligonucleotides to Probe cDNA Library

The oligonucleotide probes were 5' end-labelled with gamma-[$^{32}$P] dATP and the enzyme polynucleotide kinase (Amersham International). The method was essentially that of Woods (1982, 1984), except that a smaller amount of isotope (15 μCi) was used to label about 40 ng probe in 10 mM MgCl$_2$, 100 mM Tris-HCl. pH 7.6; 20 mM 2-mercaptoethanol.

The cDNA library was grown on GeneScreen (New England Nuclear) nylon membranes placed on the surface of L-agar+100 μg/ml ampicillin plates. (The word GeneScreen is a trade mark.) Colonies were transferred from microtitre plates to the membranes using a 6×8 multi-pronged device, designed to fit into the wells of half the microtitre plate. Colonies were grown overnight at 37° C., lysed in sodium hydroxide and bound to membranes as described by Woods (1982, 1984). After drying the membranes were washed extensively in 3×SSC/0.1% SDS at 65° C. and hybridised to the labelled probe, using a HYBAID apparatus from Hybaid Ltd, PO Box 82, Twickenham, Middlesex. (The word HYBAID is a trade mark.) Conditions for hybridisation were as described by Mason & Williams (1985), a $T_d$ being calculated for each oligonucleotide according to the formula:

$$T_d = 4° \text{ C. per GC base pair} + 2° \text{ C. per AT base pair.}$$

At mixed positions the lowest value is taken.

Hybridisation was carried out at $T_d$–5° C. Washing was in 6×SSC, 0.1% SDS initially at room temperature in the HYBAID apparatus, then at the hybridisation temperature ($T_d$–5° C.) for some hours, and finally at $T_d$ for exactly 2 minutes. Membranes were autoradiographed onto FUJI X-ray film, with intensifying screens at−70° C. (The word FUJI is a trade mark.) After 24 –48 hours positive colonies stood out as intense spots against a low background.

Example 10
Analysis of Positive Clones for the 47 kD/31 kD Polypeptide

Only one positive clone. pMS600, was obtained. This released two PstI fragments on digestion of total length 1.3 kb, insufficient to encode the 67 kD precursor. The total insert was removed from the vector on a HindIII-EcoRI fragment, nick-translated and used to probe the cDNA library, picking up a further two positive clones. pMS700 and pMS800. Restriction mapping of all three inserts suggested an overlapping map covering nearly 2.0 kb, sufficient to encode the 67 kD precursor (see FIG. 1).

Example 11
Sequencing the Cloned Inserts

The sequencing strategy was to clone the inserts, and where appropriate subclones thereof, into the multiple cloning site of the plasmids pTZ18R/pTZ19R (Pharmacia). These plasmids are based on the better-known vectors pUC18/19 (Norrander et al. 1983), but contain a single-stranded origin of replication from the filamentous phage fl. When superinfected with phages in the same group, the plasmid is induced to undergo single-stranded replication, and the single-strands are packaged as phages extruded into the medium. DNA can be prepared from these 'phages' using established methods for M13 phages (Miller, 1987), and used for sequencing by the method of Sanger (1977) using the reverse sequencing primer. The superinfecting phage used is a derivative of M13 termed M13K07, which replicates poorly and so does not compete well with the plasmid, and contains a selectable kanamycin-resistance marker. Detailed methods for preparing single-strands from the pTZ plasmids and helper phages are supplied by Pharmacia. DNA sequence was compiled and analysed using the Staden package of programs (Staden, 1986), on a PRIME 9955 computer. (The word PRIME is a trade mark.)

Example 12
Features of the 47 kD/31 kD cDNA and Deduced Amino-acid Sequence of the 67 kD Precursor DNA sequencing of the three positive clones. pMS600, pMS700, pMS800, confirmed the overlap presumed in FIG. 1. No sequence differences were found in the overlapping regions (about 300 bp altogether), suggesting that the three cDNAs were derived from the same gene. The sequence of the combined cDNAs comprising 1818 bases is shown in FIG. 2. The first ATG codon is found at position 14, and is followed by an open reading frame of 566 codons. There is a 104-base 3' untranslated region containing a polyadenylation signal at position 1764. The oligonucleotide probe sequence is found at position 569.

The open reading frame translates to give a polypeptide of 566 amino-acids (FIG. 2), and a molecular weight of 65612, which is reasonably close to the 67 kD measured on SDS-PAGE gels. The N-terminal residues are clearly hydrophobic and look like a characteristic signal sequence. Applying the rules of Von Heije (1983), which predict cleavage sites for signal sequences, suggests a cleavage point between amino-acids 20 and 21 (see FIG. 3). The region following this is highly hydrophobic and contains four Cys-X-X-X-Cys motifs.

The N-terminus of the mature protein has been roughly identified as the glutamate (E) residue at 135 (FIG. 3), on the basis of some tentative N-terminal sequence (SEQ ID NO:3) (EEPGSQFANPAYHF). This N-terminus would give a mature protein of 49068 kD, in rough agreement with that observed. There appears to be no glycosylation sites (Asn-X-Ser/Thr) in the mature protein of the sequence.

Homologies Between the 67 kD Precursor and Other Known Proteins

Searches through the PIR database, and through the literature, revealed close homologies between the 67 kD polypeptide and a class of seed storage proteins termed vicilins, one of two major classes of globulins found in seed (Borroto and Dure, 1987). Alignments between the 67 kD polypeptide and vicilins from cotton (*Gossypium hirsutum*, Ghi), soybean (*Glycine max*, Gma), pea (*Pisum sativum*, Psa-c is convicilin. Psa-v is vicilin) and bean (*Phaseolus vulgaris*, Pvu) are shown in FIG. 4 (Bown et al, 1988; Chlan et al, 1986; Doyle et al, 1986; Lycett et al. 1983). Identical residues are boxed.

All the vicilins have a mature molecular weight of around 47 kD, with the exception of soybean conglycinin alpha and alpha1 subunits, which are 72 kD and 76 kD respectively, and pea convicilin with a mature molecular weight of 64kD. The pea and bean subunits (2 sub classes each) are synthesised as small precursors, around 50 kD). The most striking homology with the 67 kD is the cotton vicilin (Chlan et al, 1986). Cotton is also the most closely related to cocoa: both are members of the order Malvales. Interestingly cotton also has a large precursor, of 69 kD, comprising a short signal sequence, a large hydrophilic domain containing six Cys-X-X-X-Cys motifs, and a mature domain. It may therefore be possible to synthesise the corresponding cotton protein, by techniques analogous to those disclosed in this application and to use the cotton protein, or fragments of it, in the preparation of flavour components analogous to cocoa flavour components.

Example 13
Expression of the 67 kD Polypeptide in *E. coli*

Figure 6:
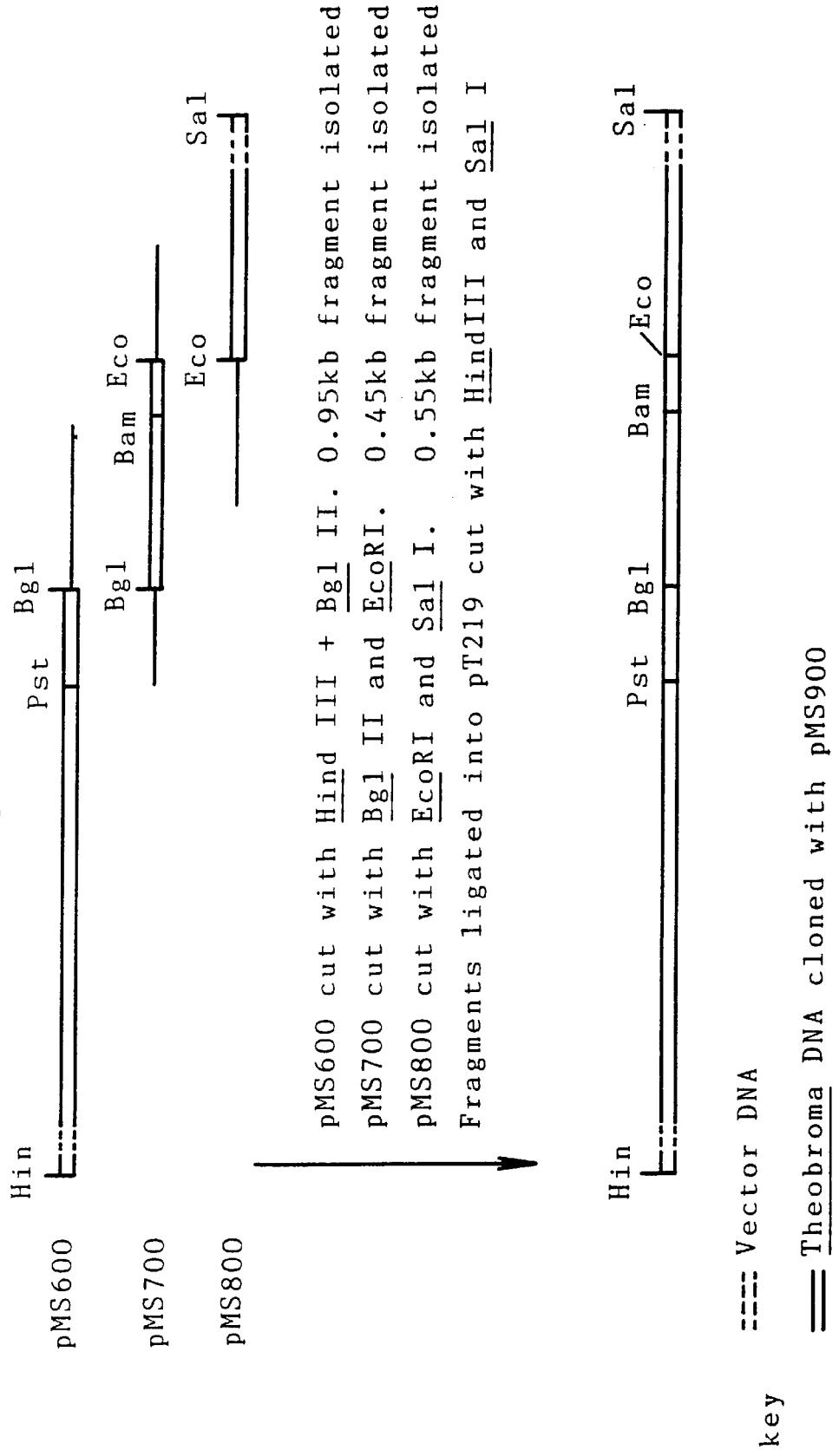
FIG. 6 shows schematically the formation of plasmid pMS900.

Before the 67 kD coding region could be inserted into a expression vector the overlapping fragments from the three separate positive clones had to be spliced into a continuous DNA segment. The method of splicing is illustrated in FIG. 6: a HindIII-BglII fragment from pMS600, a BglII-EcoRI fragment from pMS700 and an EcoRI-SalI fragment from pMS800 were ligated into pTZ19R cut with HindIII and SalI. The resulting plasmid, containing the entire 67 kD cDNA, was termed pMS900.

An NcoI site was introduced at the ATG start codon, using the mutagenic primer: (SEQ ID NO:20)

5' TAG CAA CCA TGG TGA TCA 3'.

In vitro mutagenesis was carried out using a kit marketed by Amersham International, which used the method of Eckstein and co-workers (Taylor et al, 1985). After annealing the mutagenic primer to single-stranded DNA the second strand synthesis incorporates alpha-thio-dCTP in place of dCTP. After extension and ligation to form closed circles, the plasmid is digested with NciI, an enzyme which cannot nick DNA containing thio-dC. Thus only the original strand is nicked, and subsequently digested with exonuclease III. The original strand is then resynthesised, primed by the remaining DNA fragments and complementing the mutated position in the original strand. Plasmids are then transformed into *E. coli* and checked by plasmid mini preparations.

Figure 5:
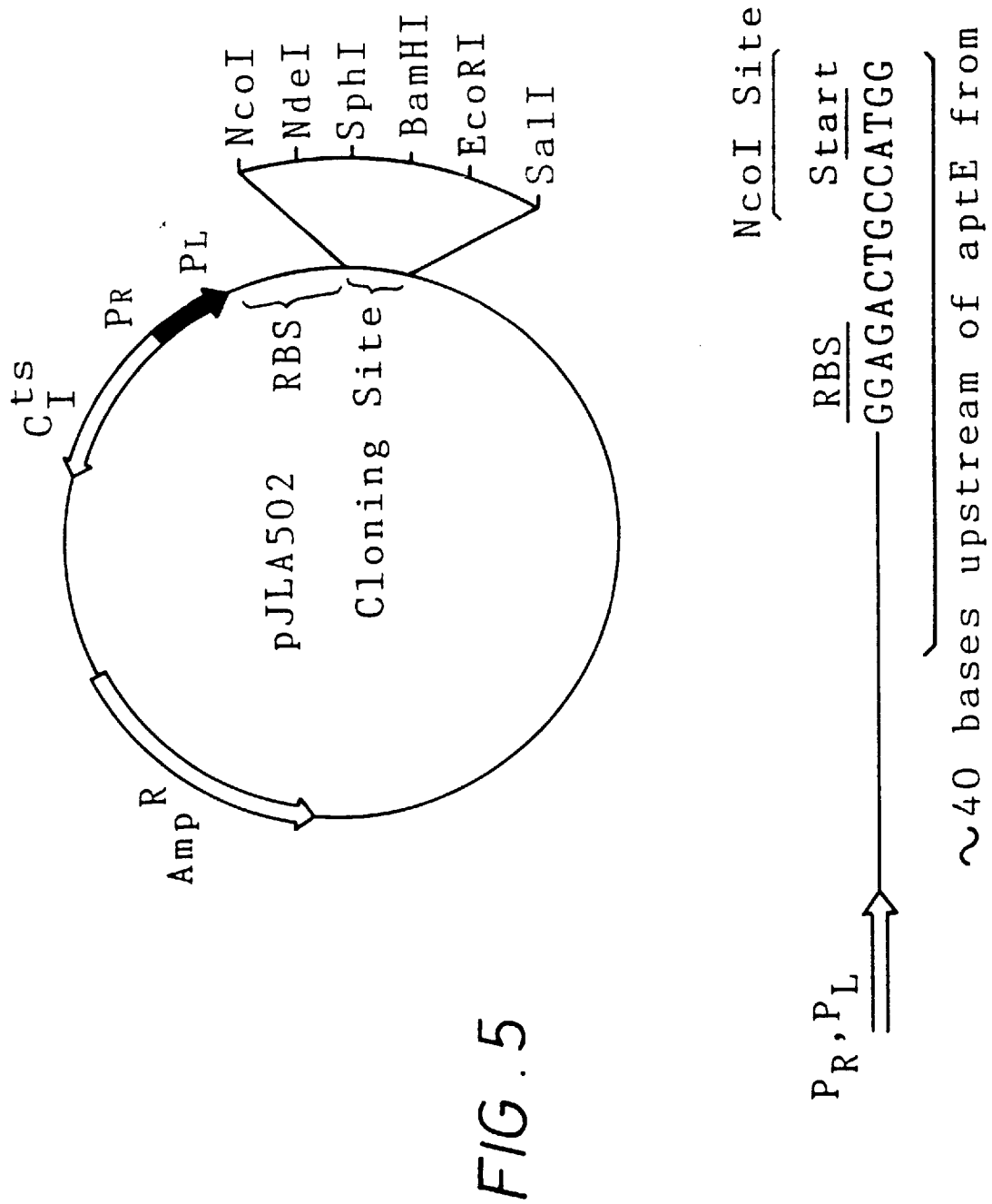
FIG. 5 (SEQ ID NO:28) shows a map of plasmid pJLA502.

The 67 kD cDNA was then cloned into the *E. coli* expression plasmid, pJLA502 (FIG. 5), on an NcoI-SalI fragment (pMS902). pJLA502 (Schauder et al, 1987) is marketed by Medac GmbH, Postfach 303629, D-7000, Hamburg 36 and contains the strong lambda promoters, $P_L$ and $P_R$, and the leader sequence and ribosome binding site of the very efficiently translated *E. coli* gene, atpE. It also contains a temperature-sensitive cI repressor, and so expression is repressed at 30° C. and activated at 42° C. The vector has an NcoI site (containing an ATG codon: CCATGG) correctly placed with respect to the ribosome binding site, and foreign coding sequences must be spliced in at this point.

The expression vector was transformed into *E. coli* UT580. The transformed strain was grown in L-broth+ ampicillin (100 μg/ml) at 30° C. until log phase ($OD_{610}$=0.5) and the temperature was then shifted to 42° C. and samples taken at intervals. Samples were dissociated by boiling in SDS loading buffer, and run on SDS-PAGE gels. The proteins were electroblotted onto nitrocellulose membranes (Towbin et al. 1979) and Western blotting carried out using the anti-21 kD antibody prepared in Example 3 above (at 2 μg/ml) and as a secondary antibody, goat anti-rabbit-IgG conjugated to alkaline phosphatase (Scott et al, 1988).

A specific band at 67 kD was produced by pMS902, showing that a functional gene was present.

Example 14
Expression of the 67 kD Polypeptide in Yeast

Two yeast expression vectors were used, both based on a yeast-E. coli shuttle vector containing yeast and E. coli origins of replication, and suitable selectable markers (ampicillin-resistance for E. coli and leucine auxotrophy for yeast). Both vectors contain the yeast pyruvate kinase (PK) promoter and leader sequence and have a HindIII cloning site downstream of the promoter. One vector, A (YVA), is designed for internal expression, and the other, B (YVB), for secreted expression, having a portion of the signal sequence of the yeast mating alpha-factor downstream of the promoter, with a HindIII site within it to create fusion proteins with incoming coding sequences. The vectors are illustrated in FIG. 7.

To use the vectors effectively it is desirable to introduce the foreign coding region such that for vector A, the region from the HindIII cloning site to the ATG start is the same as the yeast PK gene, and for vector B, the remainder of the alpha-factor signal, including the lysine at the cleavage point. In practice this situation was achieved by synthesising two sets of HindIII- NcoI linkers to breach the gap between the HindIII cloning site in the vector and the NcoI at the ATG start of the coding sequence. This is illustrated in FIG. 8.

In order to use the yeast vector B, the hydrophobic signal sequence must first be deleted from the 67 kD cDNA. Although direct evidence of the location of the natural cleavage site was lacking, the algorithm of Von Heije predicts a site between amino-acids 20 (alanine) and 21 (leucine). However it was decided to remove amino-acids 2–19 by deletion, so that the useful NcoI site at the translation start would be maintained.

For ease of construction of the yeast vectors, the strategy was to first clone the HindIII- NcoI linkers into the appropriate pTZ plasmids, and then to clone the linkers plus coding region into the yeast vectors on HindIII-BamHI fragments. However the coding region contains an internal BamHI which must be removed by in vitro mutagenesis, giving a new plasmid pMS903. The signal sequence was deleted from pMS903 using the mutagenic primer (SEQ ID NO:21)

5'AGCATAGCAACCATGGTTGCTTTGTTCT 3' to give pMS904. The appropriate HindIII- NcoI linkers were then cloned into pMS903 and pMS904 to give pMS907 and pMS905 respectively, and the HindIII- BamHI fragments (linkers+coding region) subcloned from these intermediate plasmids into YVA and YVB respectively to give the yeast expression plasmids pMS908 and pMS906. A diagrammatic scheme for these and other constructs is given in FIG. 9.

Figure 9A:
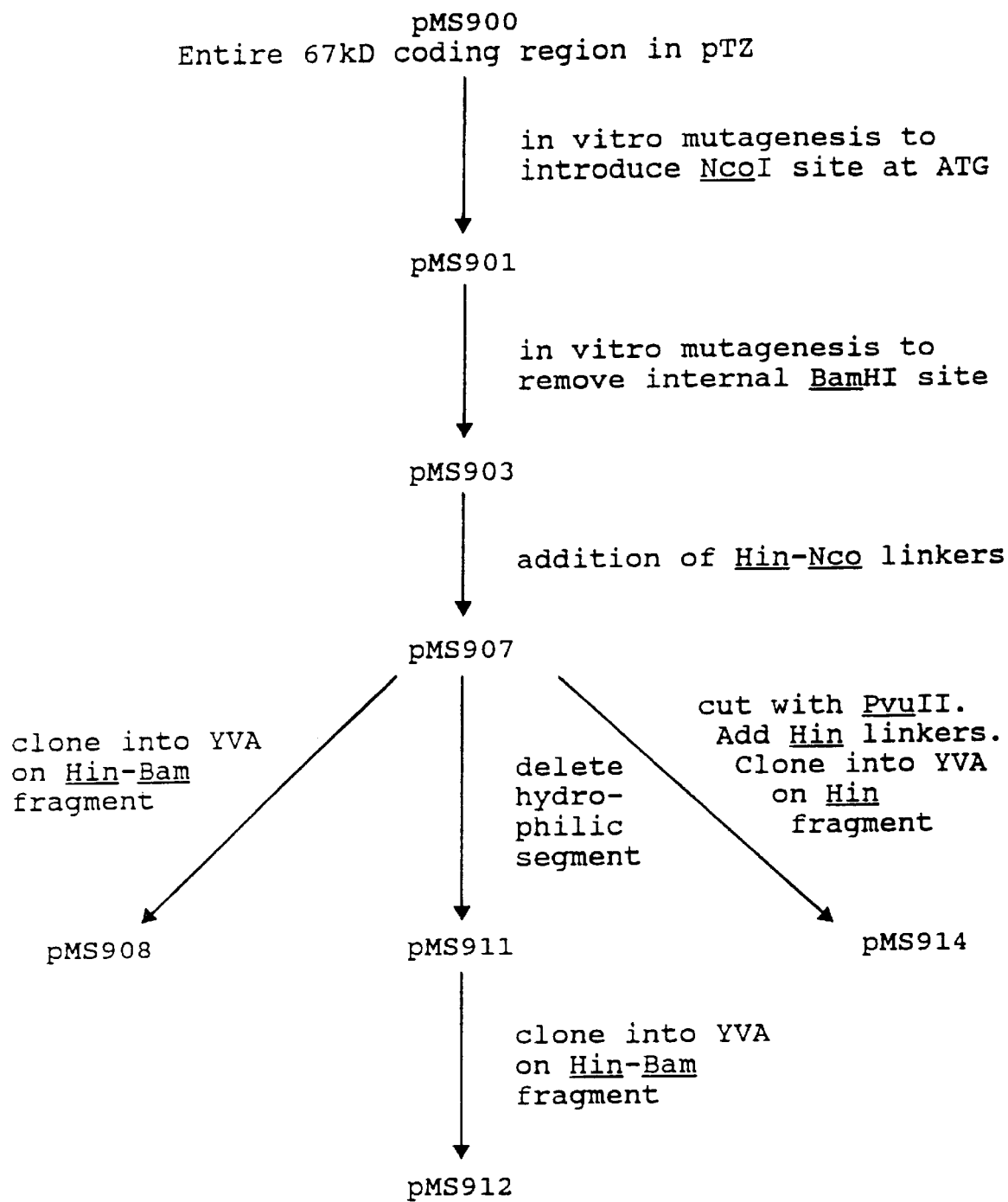
FIG. 9a shows how plasmid pMS900 can be manipulated to produce plasmids pMS901, pMS903, pMS907, pMS908, pMS911, pMS912 and pMS914.

Because the mature cocoa protein appears to lack the N-terminal hydrophilic domain, as described in Example 12, expression vectors have also been designed to express the mature protein directly. Yeast is unlikely to have the same processing enzymes as cocoa and optimum expression may be obtained for a protein as close as possible to that found naturally in cocoa. Hence the DNA encoding the hydrophilic domain (amino acids 20–134) was deleted from the intermediate plasmids pMS907 and pMS905 to give plasmids pMS911 and pMS909 respectively, and the HindIII- BamHI fragments for these were cloned into YVA and YVB to give the expression plasmids pMS912 and pMS910 (FIG. 9).

A further modification was introduced by constructing expression in which the plant terminator had been removed and replaced with the yeast ADH terminator (present in YVA and YVB). The plant signal was removed by cutting the intermediate plasmids pMS907 and pMS905 at the PvuII site immediately downstream of the coding region, at position 1716 in FIG. 2. HindIII linkers were added and the entire coding region cloned into the yeast expression vectors on HindIII- HindIII fragments giving expression plasmids pMS914 (YVA) and pMS916 (YVB) (FIG. 9). A summary of the constructs made is given in FIG. 10.

The yeast expression plasmids were transferred into yeast spheroplasts using the method of Johnston (1988). The transformation host was the LEU$^{31}$ strain AH22, and transformants were selected on leucine-minus minimal medium. LEU$^{30}$ transformants were streaked to single colonies, which were grown in 50 ml YEPD medium (Johnston. 1988) at 28|C for testing the extent and distribution of foreign protein. Cells were harvested from cultures in preweighed tubes in a bench-top centrifuge, and washed in 10 ml lysis buffer (200 mM Tris. pH 8.1:10% glycerol). The cell medium was reserved and concentrated 10–25×in an AMICON mini concentrator. (The word AMICON is a trade mark.) The washed cells were weighed and resuspended in lysis buffer plus protease inhibitors (1 mM phenyl methyl sulphonyl fluoride (PMSF); 1 μg/ml aprotinin; 0.5 μg/ml leupeptin) at a concentration of 1 g/ml. 1 volume acid-washed glass-beads was added and the cells broken by vortexing for 8 minutes in total, in 1 minute bursts, with 1 minute intervals on ice. After checking under the microscope for cell breakage, the mixture was centrifuged at 7000 rpm for 3 minutes to pellet the glass beads. The supernatant was removed to a pre-chilled centrifuge tube, and centrifuged for 1 hour at 20,000 rpm. (Small samples can be centrifuged in a microcentrifuge in the cold.) The supernatant constitutes the soluble fraction. The pellet was resuspended in 1 ml lysis buffer plus 10% SDS and 1% mercaptoethanol and heated at 90° C. for 10 minutes. After centrifuging for 15 minutes in a microcentrifuge the supernatant constitutes the particulate fraction.

Samples of each fraction and the concentrated medium were examined by Western blotting. Considering first the plasmids designed for internal expression in YVA, pMS908 produced immunoreactive proteins at 67 kD and 16 kD within the cells only. There was no evidence of the 67 kD protein being secreted under the influence of its own signal sequence. The smaller protein is presumed to be a degradation product. A similar result, but with improved expression, was obtained with pMS914, in which the plant terminator is replaced by a yeast terminator. However in pMS912, in which the coding region for the hydrophilic domain has been deleted, no synthesis of immunoreactive protein occurred.

For industrial production of heterologous proteins in yeast a secreted mode is preferable because yeast cells are very difficult to disrupt, and downstream processing from total cell protein is not easy. The results from the vectors constructed for secreted expressed were rather complicated. From the simplest construct, pMS906, in which the yeast α-factor signal sequence replaces the plant protein's own signal, immunoreactive proteins of approximately 47 kD, 28 kD and 18–20 kD were obtained and secreted into the medium. At first sight this is surprising because the coding region introduced should synthesise a 67 kD protein. However the most likely explanation is that the yeast's KEX2 protease, that recognises and cleaves the α-factor signal at a Lys-Arg site is also cleaving the 67 KD protein at Lys-Arg dipeptides at positions 148 and 313 in the amino-acid sequence. The calculated protein fragment sizes resulting from cleavage at these positions are 47179 Daltons, 28344 Daltons and 18835 Daltons, very close to the observed sizes.

When the plant terminator is replaced with a yeast terminator in pMS916 no expression is obtained in either cells or medium; it is possible that a mutation has been inadvertently introduced. From the construct pMS910, in which the hydrophilic domain has been deleted the main antigenic products were 28 KD and 18–20 kD, again secreted into the medium. It is presumed that the de novo 47 kD product is immediately cleaved at the KEX2 site at position 313.

In summary, four of the six expression vectors constructed direct the synthesis of proteins cross-reacting with anti-47 kD antibodies. Two of the constructs secrete proteins into the medium.

Example 15

Construction of Vectors Designed to Express the 67 kD Protein in *Hansenula polymorpha*

The methylotropic yeast *Hansenula polymorpha* offers a number of advantages over *Saccharanyces cerevisiae* as a host for the expression of heterologous proteins (EP-A-0173378 and Sudbery et al, 1988). The yeast will grow on methanol as sole carbon source, and under these conditions the enzyme methanol oxidase (MOX) can represent up to 40% of the total cell protein. Thus the MOX promoter is a very powerful one that can be used in a vector to drive the synthesis of heterologous proteins, and it is effective even as a single copy. This gives the potential to use stable integrated vectors. *Hansenula* can also grow on rich carbon sources such as glucose, in which case the MOX promoter is completely repressed. This means that cells containing the heterologous gene can be grown to a high density on glucose, and induced to produce the foreign protein by allowing the glucose to run out and adding methanol.

Figure 11B:
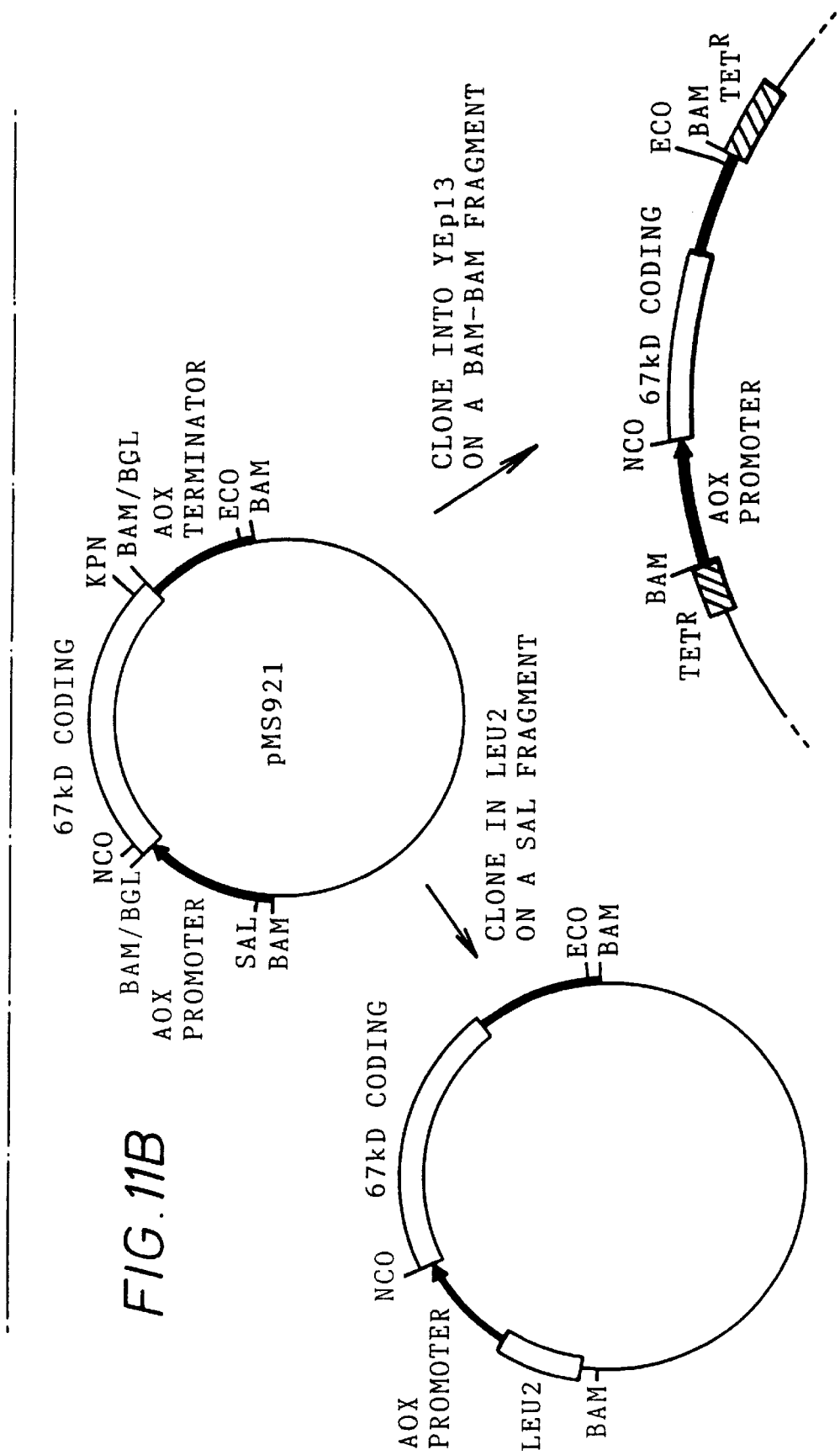
FIG. 11 shows the construction of a plasmid to express the 67 kD protein by means of the AOX promoter on an integrated vector in *Hansenula polymorpha*.
Figure 12A:
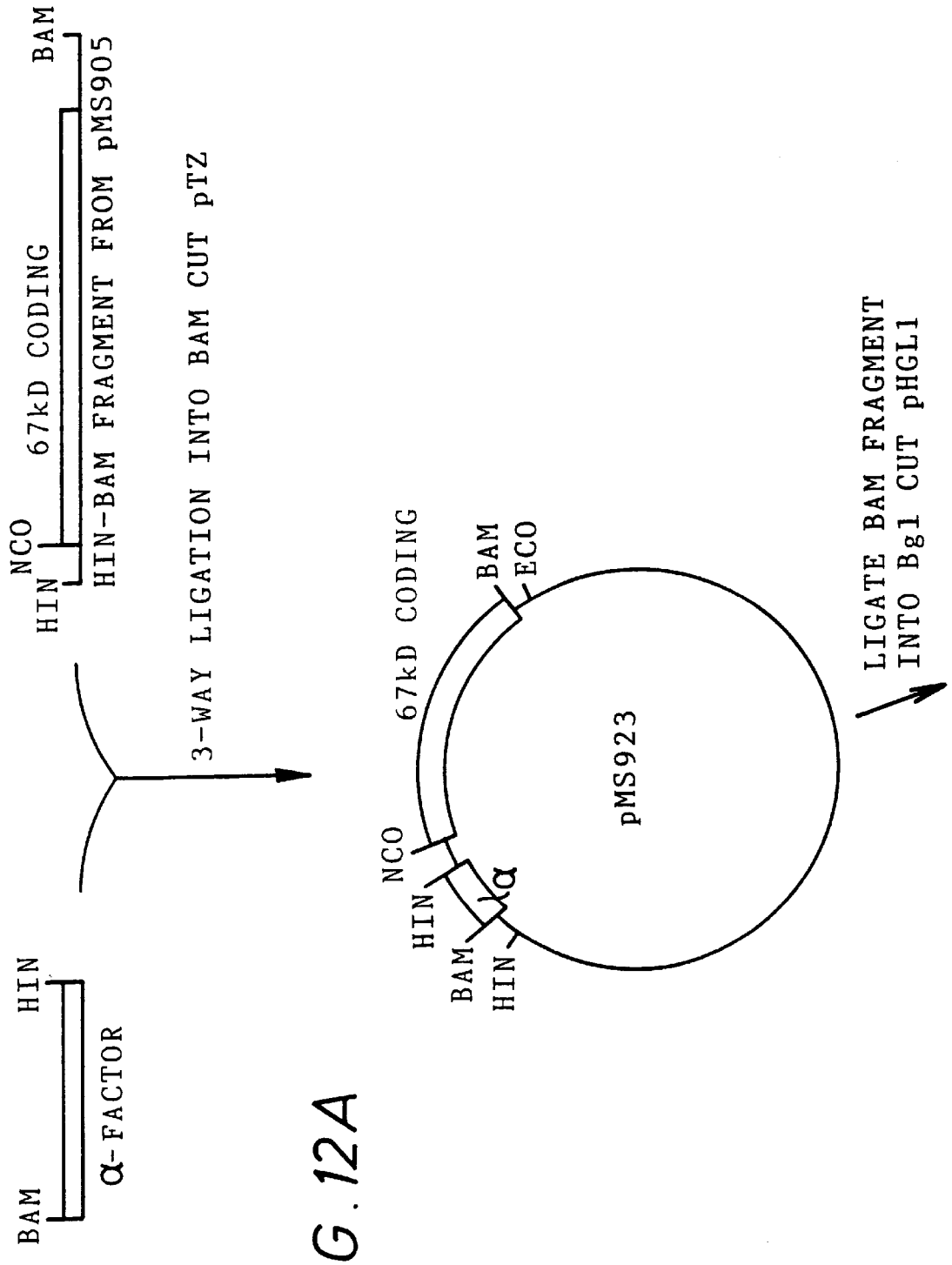
FIG. 12 shows the construction of a plasmid to express the 67 kD protein by means of the AOX promoter in conjunction with the yeast α-factor secretory signal on an integrated vector in *Hansenula polymorpha*.

A plasmid, pHGL1, containing the MOX promoter and terminator, and a cassette containing the yeast α-factor secretory signal sequence, were prepared. The 67 kD coding region was cloned into pHGL1 on a BamHI—BamHI fragment, replacing the BglII fragment which contains the 3' end of the MOX coding region. The whole promoter—gene—terminator region can then be transferred to YEp13 on a BamHI—BamHI fragment to give the expression plasmid pMS922. The details of the construction are illustrated in FIG. 11. An analogous expression plasmid, pMS925, has been constructed with the yeast α-factor spliced onto the 67 kD coding region, replacing the natural plant signal. The BamHI-HindIII cassette containing the α-factor was ligated to the HindIII-BamHI fragment used to introduce the 67 kD coding region into YVB. The α-factor plus coding region was then cloned with pHGL1 on a BamHI—BamHI fragment, and transferred into YEP13 as before. Details are shown in FIG. 12.

Both constructs have been transformed into Hansenula and grown under inducing conditions with 0.5 % or 1% methanol. Both constructs directed the production of immunoreactive protein within the cells, and pMS925 secreted the protein into the medium under the influence of the α-factor signal sequence.

*E. coli* Strains

RR1 $F^{31}v_B{}^{31}M_B$ ara-14 proA2 leuB6 lacY1 galK2 vpsL20 (str$^r$) xyl-5 mtl-1 supE44$^{31}$ CAG629 lac$_{am}$ tvp$_{am}$ Pho$_{am\ htpRam}$ mal rpsL lon supC$_{ts}$ UT580 (lac-pro) supE thi hsdD5/F'tra D36 proA$^{30}$B$^{30}$ lacI$^q$ lacZ M15

References

Aviv, H., and Leder. P. *Proc. Natl. Acad. Sci. USA* 69, 1408–1412 (1972). Purification of biologically active globin mRNA by chromatography on oligo dT cellulose Biehl, B., Wewetzer, C., and Passern. D. J. *Sci. Food Agric.* 33, 1291–1304 (1982). Vacuolar (Storage) Proteins of Cocoa Seeds and their Degradation during Germination and Fermentation.

Borroto, K., and Dure, L. *Plant Molecular Biology* 8, 113–131 (1987). The globulin seed storage proteins of flowering plants are derived from two ancestral genes.

Bown, D., Ellis, T. H. N., and Gatehouse, J. A. *Biochem. J.* 251, 717–726 (1988). The sequence of a gene encoding convicilin from pea (*Pisum sativum*) shows that convicilin differs from vicilin by an insertion near the N-terminus.

Catty, D. and Raykundalia. C. Production and Quality control of Polyclonal Antibodies in: "Antibodies: A Practical Approach" Vol I, IRL Press (1988)

Chlan, C. A., Pyle, J. B., Legocki, A. B., and Dure, L. *Plant Molecular Biology* 7, 475–489 (1986). Developmental biochemistry of cotton seed embryogenesis and germination XVIII. cDNA and amino acid sequences of members of the storage protein families.

Cuming, A. C., Williams, R. S., and Cullimore, J. V. in "Immunology in Plant Science", Ed. Wang, T. L., Cambridge University Press, 1986. The use of Antibodies in Molecular Biology.

Doyle, J. J., Schuler, M. A., Godette, W. D., Zencer, V., Beachy, R. N., and Slightom, J. L. *J. Biol. Chem.* 261, 9228–9238 (1986). The glycosylated seed storage proteins of Glycine max and Phaseolus vulgaris: Structural homologies of genes and proteins.

Dretzen, G., Bellard, M., Sassone-Corsi, P., and Chambon, P. *Analytical Biochemistry* 112, 29514 298 (1981). A reliable method for the recovery of DNA fragments from agarose and acrylamide gels.

Eschenfeldt, W. H., Puskas, R. S., and Berger, S. L. *Methods in Enzymology* 152, 337–342 (1987). Homopolymeric Tailing.

Fritz et al (*J. Food Sci.* 50 946–950 (1985))

Gubler, U., and Hoffman, 3.J. *Gene* 25, 263 (1983). A simple and very efficient method for generating cDNA libraries.

Hall, T. C., Ma. Y., Buchbinder, B. U., Pyrne J. W., Sun, S. M., and Bliss, F. A. *Proc. Natl. Acad. Sci. USA* 75, 3196–3200 (1978). Messenger RNA for Gl protein of French bean seeds: cell-free translation and product characterisation.

Hill, S. A. "Methods in Plant Virology", Blackwell 1984.

Johnston, J. R. in "Yeast: A practical approach". Eds Campbell, I., and Duffus, J. H. IRL Press, 1988. Yeast Genetics, Molecular Aspects.

Kreil, G. *Annual Rev. Biochem.* 50, 317–348 (1981). Transfer of proteins across membranes.

Laemmli, U. K. *Nature* 227, 680 (1970). Cleavage of structural proteins during the assembly of the head of bacteriophage T4.

Lipman, D. J., and Pearson. W. R. *Science* 227, 1435–1441 (1985). Rapid protein sequence similarity searches.

Lycett, G. W., Delauney, A. J., Gatehouse. J. A., Gilroy, J., Croy, R. R. D., and Boulter, D. *Nucleic Acids Res.* 11, 2367–2380 (1983).

Maniatis. T., Fritsch, E. F., and Sambrook, J. "Molecular Cloning: A Laboratory Manual", Cold Spring Harbour Laboratory, 1982.

Mason, P. J., and Williams. J. G. in "Nucleic Acid Hybridisation: A Practical Approach". Ed. Hames, B. D., and Higgins, S. J. IRL Press 1985. Hybridisation in the Analysis of Recombinant DNA.

Meinkoth, J., and Wahl, G. M. *Analytical Biochemistry* 138, 267 (1984). Methods of Southern blotting and DNA probing.

Miller, H. *Methods in Enzymology* 152, 145–170 (1987). Practical Aspects of Preparing Phage and Plasmid DNA: Growth, Maintenance and Storage of Bacteria and Bacteriophage.

Norrander, J., Kempe. T., and Messing, J. *Gene* 26, 101 (1983). Construction of improved M13 vectors using oligodeoxynucleotide-directed mutagensis.

Proudfoot, N. J., and Brownlee, G. G. *Nature* 263, 211–214 (1976). 3' Non-coding region sequences in enkayotic messenger RNA.

Roberts, B. E., and Paterson, B. M. *Proc. Natl. Acad. Sci. USA* 70, 2330 (1973). Efficient translation of tobacco mosaic virus RNA and rabbit globin 9S RNA in a cell-free system from commercial wheat germ.

Sanger, F., Nicklen, S., and Coulson, A. R. *Proc. Natl. Acad. Sci. USA* 74, 5463–5467 (1977). DNA sequencing with chain-terminating inhibitors.

Schauder. B., Blocker, H. Frank. R., and McCarthy, J. E. G. *Gene* 52, 279–283 (1987). Inducible expression vectors incorporating the *E. coli* aptE translation initiation region.

Scott, R., Draper, J., Jefferson, R., Dury, G., and Jacob, L. in "Plant Genetic Transformation and Gene Expression: A Laboratory Manual". Eds. Draper, J., Scott, R., Armitage, P., Walden, R. Blackwell 1988. Analysis of gene organisation and expression in plants.

Staden, R. *Nucleic Acids Res.* 14, 217–231 (1986). The current status and portability of our sequence handling software.

Sudbery, P. E., Gleeson, M. A., Veale, R. A., Lederboer, A. M., and Zoetmulder, M. C. M. *Biocem. Soc. Trans* 16 1081–103 (1988). Hansenula *polymorpha* as a novel yeast system for the expression of heterologous genes.

Taylor, J. W., Ott. J., and Eckstein. F. *Nucleic Acids Res.* 13, 8765–8785 (1985). The rapid generation of oligonucleotide-directed mutations at high frequency using phosphorothioate-modified DNA.

Towbin, H., Staehelin, T., and Gordon, J. Proc. *Natl. Acad. Sci. USA* 76, 4350–4534 (1979). Electrophoretic transfer of proteins from polyacrylamide gels to nitrocellulose sheets: procedure and some applications.

Von Heije, G. *Eur. J. Biochem* 133, 17–21 (1983). Patterns of Amino-acids near Signal-Sequence Cleavage Sites.

Wahl, G. M., and Berger, S. L. *Methods in Enzymology* 152, 415–423 (1987). Screening Colonies or Plaques with Radioactive Nucleic Acid Probes. Woods, D. E. *Focus (Bethesda Research Labs)* 6, 3 (1984). Oligonucleotide Screening of cDNA Libraries.

Woods. D. E., Markham, A. F., Ricker, A. T., Goldberger, G., and Colten, H. R. *Proc. Natl. Acad. Sci. USA* 79, 5561 (1982).

---

We claim:

1. An isolated and purified 67 kD protein of *Theobroma cacao*, having the amino acid sequence shown in FIG. 3 (SEQ ID NO:22).

2. A protein as claimed in claim 1 which is recombinantly produced.

3. An isolated and purified 47 kD protein of *Theobroma cacao* produced from a protein as claimed in claim 2.

4. An isolated and purified 31 kD protein of *Theobroma cacao* produced from a protein as claimed in claim 2.

5. Recombinant or isolated nucleic acid coding for a protein as claimed in claim 1.

6. Nucleic acid as claimed in claim 5 which is DNA.

7. Nucleic acid claimed in claim 5, which is in the form of a vector.

8. Nucleic acid as claimed in claim 7, wherein the vector is an expression vector and the protein-coding sequence is operably linked to a promoter.

9. Nucleic acid as claimed in claim 8, wherein the expression vector is a yeast expression vector and the promoter is a yeast pyruvate kinase (PK) promoter.

10. Nucleic acid as claimed in claim 8, wherein the expression vector is a bacterial expression vector and the promoter is a strong lambda promoter.

11. Nucleic acid as claimed in claim 8, comprising a signal sequence.

12. A host cell comprising nucleic acid as claimed in claim 7.

13. A host cell as claimed in claim 12 which is *Saccharomyces cerevisiae*.

14. A host cell as claimed in claim 12 which is *E. coli*.

* * * * *

UNITED STATES PATENT AND TRADEMARK OFFICE
CERTIFICATE OF CORRECTION

PATENT NO. : 5,770,433

DATED : June 23, 1998

INVENTOR(S): MARGARET ELIZABETH SPENCER, ET AL.

It is certified that error appears in the above-identified patent and that said Letters Patent is hereby corrected as shown below:

In the drawings;

SHEET 13
 Fig. 7, "PROMOTOR" should read --PROMOTER--.

Figure 12B:
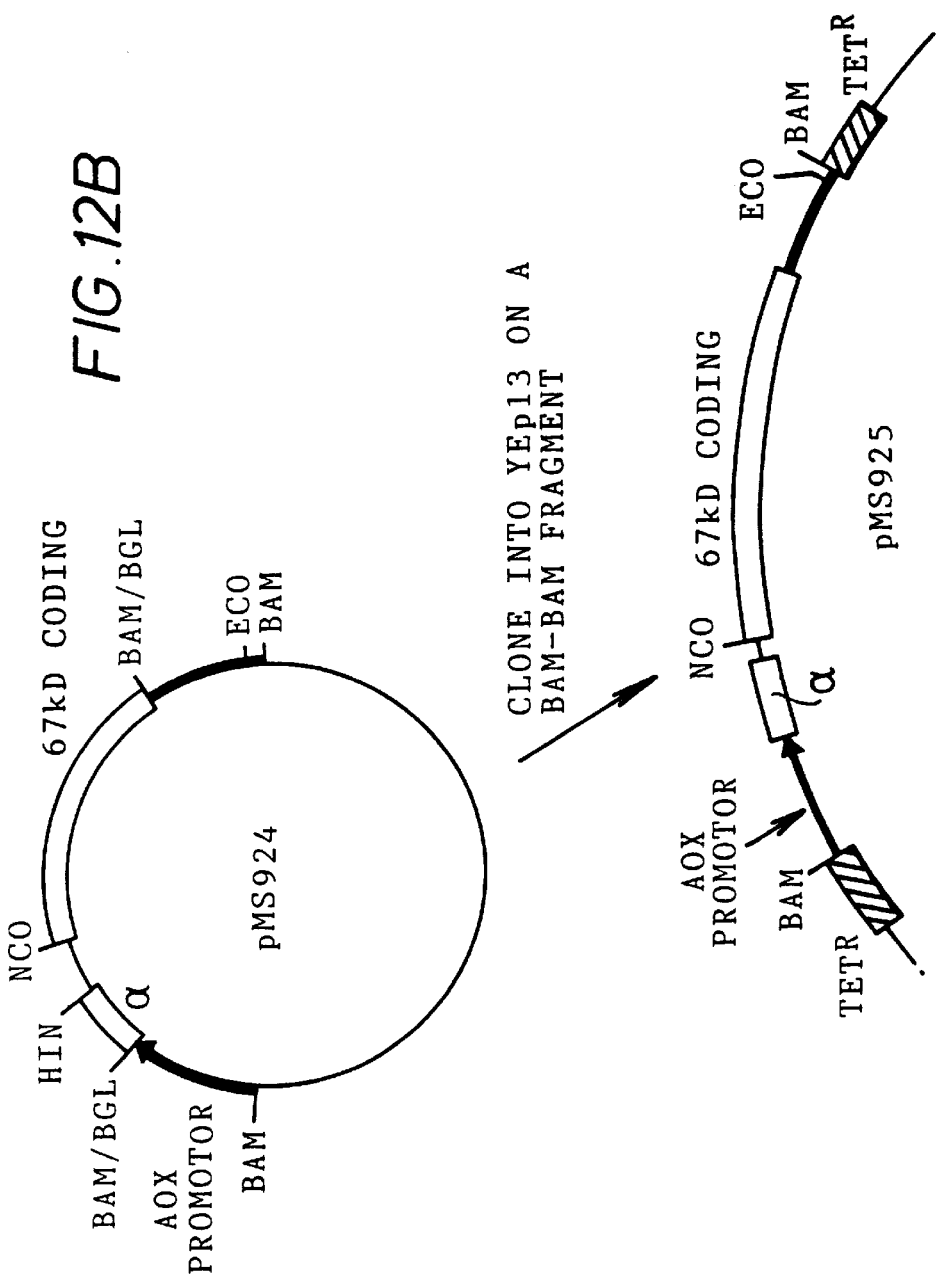

SHEET 22
 Fig. 12B, "PROMOTOR" should read --PROMOTER--.

COLUMN 1
 Line 5, "PCT/G891/00914" should read --PCT/GB91/00914--.

COLUMN 1
 Line 25, "Germination." should read --germination.--.

COLUMN 2
 Line 63, "shows" should read --show--.

COLUMN 3
 Line 1, "shows" should read --respectively show--;
 Line 4, "5" should read --5 which includes--.

COLUMN 5
 Line 19, "phosphate pH" should read --phosphate;--.

COLUMN 6
 Line 33, "3kD" should read --31kD--.

UNITED STATES PATENT AND TRADEMARK OFFICE
CERTIFICATE OF CORRECTION

PATENT NO. : 5,770,433

DATED : June 23, 1998

INVENTOR(S): MARGARET ELIZABETH SPENCER, ET AL.

Page 2 of 3

It is certified that error appears in the above-identified patent and that said Letters Patent is hereby corrected as shown below:

<u>COLUMN 10</u>
Line 24, "a" should read --an--;
Line 34, "primer: (SEQ ID NO: 20)" should read --primer (SEQ ID NO: 20):--.

<u>COLUMN 11</u>
Line 30, "breach" should read --bridge--.

<u>COLUMN 12</u>
Line 16, "LEU$^{31}$" should read --LEU$^-$--;
Line 19, "LEU$^{30}$" should read --LEU$^+$--;
Line 21, "28/C" should read --28°C--;
Line 60, "expressed" should read --expression--.

<u>COLUMN 13</u>
Line 63, "F$^{31}$v$_B^{31}$M$_B$" should read --F$^-$v$_B$M$_B$--;
Line 64, "supE44$^{31}$" should read --supE44$^-$--;
Line 65, "Pho$_{am}$htpR$_{am}$" should read --pho$_{am}$htpR$_{am}$--;
Line 66, "proA$^{30}$B$^{30}$" should read --proA$^+$B$^+$--.

<u>COLUMN 14</u>
Line 15, "Raykundalia." should read --Raykundalia,--.
Line 33, "29514 298" should read --295-298--.
Line 40, "3.J." should read --B.J.--.

UNITED STATES PATENT AND TRADEMARK OFFICE
CERTIFICATE OF CORRECTION

PATENT NO. : 5,770,433

DATED : June 23, 1998

INVENTOR(S): MARGARET ELIZABETH SPENCER, ET AL.

Page 3 of 3

It is certified that error appears in the above-identified patent and that said Letters Patent is hereby corrected as shown below:

<u>COLUMN 15</u>
Line 12, "enkayotic" should read --eukaryotic--.

<u>COLUMN 16</u>
Line 6, "Biocem. Soc. Trans" should read --Biochem. Soc. Trans.--;
Line 7, "Hansenula" should read --*Hansenula*--.

Signed and Sealed this

Twenty-fourth Day of August, 1999

Attest:

Q. TODD DICKINSON

*Attesting Officer*   *Acting Commissioner of Patents and Trademarks*